(12) United States Patent
Lin

(10) Patent No.: US 9,932,621 B2
(45) Date of Patent: Apr. 3, 2018

(54) MODULATORS FOR SIRT5 AND ASSAYS FOR SCREENING SAME

(75) Inventor: Hening Lin, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 477 days.

(21) Appl. No.: 13/808,706

(22) PCT Filed: Jul. 7, 2011

(86) PCT No.: PCT/US2011/043130
§ 371 (c)(1),
(2), (4) Date: Jan. 7, 2013

(87) PCT Pub. No.: WO2012/006391
PCT Pub. Date: Jan. 12, 2012

(65) Prior Publication Data
US 2015/0057236 A1 Feb. 26, 2015

Related U.S. Application Data

(60) Provisional application No. 61/362,078, filed on Jul. 7, 2010.

(51) Int. Cl.
| | | |
|---|---|---|
| *C12Q 1/37* | (2006.01) |
| *A61K 31/197* | (2006.01) |
| *C12Q 1/25* | (2006.01) |
| *C12Q 1/34* | (2006.01) |
| *C07D 239/56* | (2006.01) |
| *C07D 233/70* | (2006.01) |
| *C07D 233/80* | (2006.01) |
| *C07D 233/84* | (2006.01) |
| *C07D 233/90* | (2006.01) |
| *C07D 235/04* | (2006.01) |
| *C07D 401/06* | (2006.01) |
| *C07D 405/06* | (2006.01) |
| *C07D 409/04* | (2006.01) |
| *C07D 239/70* | (2006.01) |
| *C07D 243/04* | (2006.01) |
| *C07D 471/04* | (2006.01) |
| *C07D 491/052* | (2006.01) |
| *C07D 495/04* | (2006.01) |
| *C07D 513/04* | (2006.01) |
| *C07D 285/24* | (2006.01) |
| *C07K 7/06* | (2006.01) |
| *C07K 14/47* | (2006.01) |
| *A61K 38/00* | (2006.01) |

(52) U.S. Cl.
CPC ............. *C12Q 1/37* (2013.01); *A61K 31/197* (2013.01); *C07D 233/70* (2013.01); *C07D 233/80* (2013.01); *C07D 233/84* (2013.01); *C07D 233/90* (2013.01); *C07D 235/04* (2013.01); *C07D 239/56* (2013.01); *C07D 239/70* (2013.01); *C07D 243/04* (2013.01); *C07D 285/24* (2013.01); *C07D 401/06* (2013.01); *C07D 405/06* (2013.01); *C07D 409/04* (2013.01); *C07D 471/04* (2013.01); *C07D 491/052* (2013.01); *C07D 495/04* (2013.01); *C07D 513/04* (2013.01); *C07K 7/06* (2013.01); *C07K 14/47* (2013.01); *C12Q 1/25* (2013.01); *C12Q 1/34* (2013.01); *A61K 38/00* (2013.01)

(58) Field of Classification Search
None
See application file for complete search history.

(56) References Cited

U.S. PATENT DOCUMENTS

| | | |
|---|---|---|
| 2004/0091951 A1 | 5/2004 | Schultz |
| 2006/0014705 A1 | 1/2006 | Howitz et al. |

FOREIGN PATENT DOCUMENTS

| | | | |
|---|---|---|---|
| WO | WO 2006/094239 A2 | 9/2006 | |
| WO | 2009/049018 A1 | 4/2009 | |
| WO | WO 2009/049018 * | 4/2009 | ............. A61K 31/33 |
| WO | WO 2009/058348 A1 | 5/2009 | |

OTHER PUBLICATIONS

Du et al., Science, 2011, 334, 806-809.*
Marcotte P.A. et al., "Fluorescence Assay of SIRT Protein Deacetylases Using an Acetylated Peptide Substrate and a Secondary Trypsin Reaction", *Analytical Biochemistry* 332:90-99 (2004).
International Search Report dated Mar. 23, 2012 received from the Korean Intellectual Property Office from related International Application No. PCT/US2011/043130.
Sauve A.A. et al., "The Biochemistry of Sirtuins", *Annu. Rev. Biochem.* 75:435-465 (2006).
Imai S-I et al., "Ten Years of NAD-Dependent SIR2 Family Deacetylases: Implications for Metabolic Diseases", *Trends in Pharmacological Sciences* 31(5):212-220 (2010).
Haigis M.C. et al., "Mammalian Sirtuins: Biological Insights and Disease Relevance", *Annu. Rev. Pathol. Mech. Dis.* 5:253-295 (2010).
Imai S-I et al., "Transcriptional Silencing and Longevity Protein Sir2 is an NAD-Dependent Histone Deacetylase", *Nature* 403:795-800 (Feb. 17, 2000).
Tanner K.G. et al., "Silent Information Regulator 2 Family of NAD-Dependent Histone/Protein Deacetylases Generates a Unique Product, 1-0-Acetyl-ADP-Ribose", *PNAS* 97(26):14178-14182 (Dec. 19, 2000).
Frye R.A., "Phylogenetic Classification of Prokaryotic and Eukaryotic Sir2-Like Proteins", *Biochemical and Biophysical Research Communications* 273(2):793-798 (2000).

(Continued)

*Primary Examiner* — Christina Bradley
(74) *Attorney, Agent, or Firm* — Scully Scott Murphy & Presser

(57) ABSTRACT

Sirt5, a mitochondrial Sirtuin, has been identified herein as an efficient demalonylase and desuccinylase. Disclosed herein are assays to identify Sirt5 modulators based on this robust enzymatic activity. Sirt5-specific modulators can be used study the biological function of Sirt5 and to target Sirt5 activities in treating human diseases.

15 Claims, 14 Drawing Sheets

(56) References Cited

OTHER PUBLICATIONS

Michishita E. et al., "Evolutionarily Conserved and Nonconserved Cellular Localizations and Functions of Human SIRT Proteins", *Molecular Biology of the Cell* 16:4623-4635 (Oct. 2005).

Haigis M.C. et al., "SIRT4 Inhibits Glutamate Dehydrogenase and Opposes the Effects of Calorie Restriction in Pancreatic β Cells", *Cell* 126:941-954 (Sep. 8, 2006).

Schuetz A. et al., "Structural Basis of Inhibition of the Human $NAD^+$-Dependent Deacetylase SIRT5 by Suramin", *Structure* 15:377-389 (Mar. 2007).

Liszt G. et al., "Mouse Sir2 Homolog SIRT6 is a Nuclear ADP-Ribosyltransferase", *The Journal of Biological Chemistry* 280(22):21313-21320 (2005).

Michishita E. et al., "SIRT6 is a Histone H3 Lysine 9 Deacetylase that Modulates Telomeric Chromatin", *Nature* 452:492-497 (Mar. 27, 2008).

Du J. et al., "Investigating the ADP-Ribosyltransferase Activity of Sirtuins with NAD Analogues and $^{32}$P-NAD", *Biochemistry* 48(13):2878-2890 (2009).

Fatkins D.G. et al., "$N^ε$-Thioacetyl-Lysine: A Multi-Facet Functional Probe for Enzymatic Protein Lysine $N^ε$-Deacetylation", *Bioorganic & Medicinal Chemistry Letters* 16:3651-3656 (2006).

De La Fortelle E. et al., "Maximum-Likelihood Heavy-Atom Parameter Refinement for Multiple Isomorphous Replacement and Multiwavelength Anomalous Diffraction Methods", *Methods in Enzymology* 276:472-494 (1997).

Collaborative Computational Projection, No. 4, "The CCP4 Suite: Programs for Protein Crystallography", *Acta Cryst.* D50:760-763 (1994).

Cosgrove M.S. et al., "The Structural Basis of Sirtuin Substrate Affinity", *Biochemistry* 45(24):7511-7521 (2006).

Hoff K.G. et al., "Insights into the Sirtuin Mechanism from Ternary Complexes Containing $NAD^+$ and Acetylated Peptide", *Structure* 14:1231-1240 (Aug. 2006).

Kim K-H, "Regulation of Mammalian Acetyl-Coenzyme a Carboxylase", *Annu. Rev. Nutr.* 17:77-99 (1997).

Saggerson D., "Malonyl-CoA, a Key Signaling Molecule in Mammalian Cells", *Annu. Rev. Nutr.* 28:253-272 (2008).

Sauve A.A. et al., "Chemistry of Gene Silencing: The Mechanism of $NAD^+$-Dependent Deacetylation Reactions", *Biochemistry* 40(51):15456-15463 (2001).

Hawse W.F. et al., "Structural Insights into Intermediate Steps in the Sir2 Deacetylation Reaction", *Structure* 16:1368-1377 (Sep. 10, 2008).

Frezza C. et al., "Organelle Isolation: Functional Mitochondria from Mouse Liver, Muscle and Cultured Filroblasts", *Nature Protocols* 2(2):287-295 (2007).

Kim S.C. et al., "Substrate and Functional Diversity of Lysine Acetylation Revealed by a Proteomics Survey", *Molecular Cell* 23:607-618 (Aug. 18, 2006).

Rosen R. et al., "Probing the Active Site of Homoserine Trans-Succinylase", *FEBS Letters* 577:386-392 (2004).

Nakagawa T. et al., "SIRT5 Deacetylates Carbamoyl Phosphate Sythetase 1 and Regulates the Urea Cycle", *Cell* 137:560-570 (May 1, 2009).

Gao L. et al., "Simultaneous Quantification of Malonyl-CoA and Several Other Short-Chain Acyl-CoAs in Animal Tissues by Ion-Pairing Reversed-Phase HPLC/MS", *Journal of Chromatography B* 853:303-313 (2007).

Smith B.C. et al., "Sir2 Protein Deacetylases: Evidence for Chemical Intermediates and Functions of a Conserved Histidine", *Biochemistry* 45(1):272-282 (2006).

Smith B.C. et al., "Mechanism-Based Inhibition of Sir2 Deacetylases by Thioacetyl-Lysine Peptide", *Biochemistry* 46(50):14478-14486 (2007).

Zhang Z. et al., "Identification of Lysine Succinylation as a New Post-Translational Modification", *Nature Chemical Biology* 7:58-63(Jan. 2011).

Zhao S. et al., "Regulation of Cellular Metabolism by Protein Lysine Acetylation", *Science* 327:1000-1004 (Feb. 19, 2010).

Wang Q. et al., "Acetylation of Metabolic Enzymes Coordinates Carbon Source Utilization and Metabolic Flux", *Science* 327:1004-1007 (Feb. 19, 2010).

Asaba, T. et al., "Inhibition of Human Sirtuins by in Situ Generation of an Acetylated Lysine-ADP-Ribose Conjugate" Journal of the American Chemical Society (May 27, 2009) pp. 6989-6996, vol. 131, No. 2.

Morizono, H. et al., "Acetylornithine Transcarbamylase: a Novel Enzyme in Arginine Biosynthesis" Journal of Bacteriology (Apr. 15, 2006) pp. 2974-2982, vol. 188, No. 8.

Le Roux, P. et al., "Synthesis of a New Peptide Inhibitors of the Meso0Diaminopimelate-Addign Enzyme" European journal of Medicinal Chemistry (Dec. 1, 1992) pp. 899-907, vol. 27, No. 9.

Suzuki, T. et al., "Identification of a Cell-Active Non-Peptide Sirtuin Inhibitor Containing N-thioacetyl Lysine" Bioorganic & Medicinal Chemistry Letters (Oct. 1, 2009) pp. 5670-5672, vol. 19, No. 19.

He, B. et al., "Thiosuccinyl Peptides as Sirt5-Specific Inhibitors" Journal of the American Chemical Society (Feb. 1, 2012) pp. 1922-1925, vol. 134, No. 4.

Du, J. et al., "Sirt5 is a NAD-Dependent Protein Lysine Demalonylase and Desuccinylase" Science (Nov. 11, 2011) pp. 806-809, vol. 334, No. 6057.

Supplementary European Search Report dated Oct. 15, 2013 issued in European Application No. EP 11804316.

\* cited by examiner

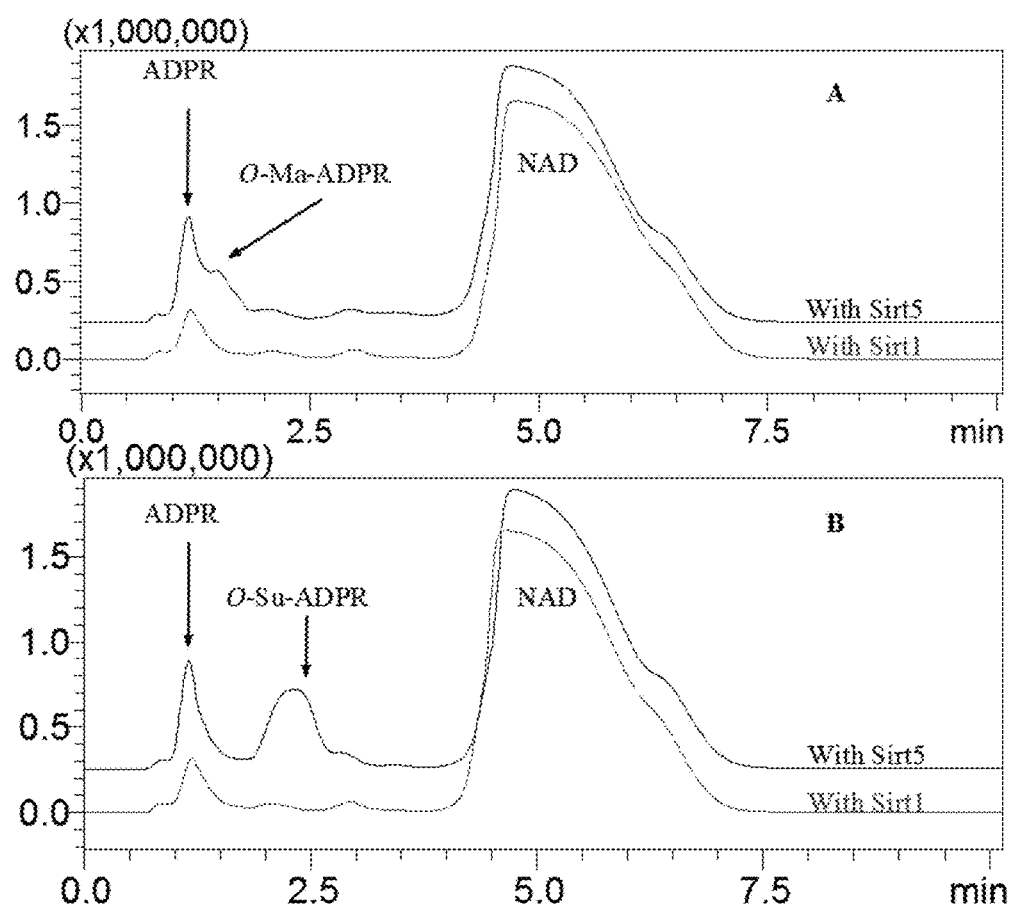
Fig. 7A-B

Demalonylation and Desuccinylation:

malonyl: n = 1
succinyl: n = 2

MODULATORS FOR SIRT5 AND ASSAYS FOR SCREENING SAME

CROSS-REFERENCE TO RELATED APPLICATIONS

This application claims priority from U.S. Provisional Application No. 61/362,078, filed Jul. 7, 2010, which is herein incorporated by reference in its entirety.

STATEMENT REGARDING FEDERALLY SPONSORED RESEARCH

This invention was made with government support under Contract No. GM086703 awarded by the National Institutes of Health. The government has certain rights in the invention.

BACKGROUND OF THE DISCLOSURE

Silent Information Regulator 2 (Sir2) proteins, or Sirtuins, are a family of evolutionarily conserved enzymes with nicotinamide adenine dinucleotide (NAD)-dependent protein deacetylase activity (A. A. Sauve, et al., *Annu. Rev. Biochem.* 75:435 (2006); S.-i. Imai, et al., *Trends in Pharmacological Sciences* 31:212 (2010); M. C. Haigis, et al., *Annual Review of Pathology: Mechanisms of Disease* 5:253 (2010)). Since the initial discovery of sirtuin deacetylase activity (S.-i. Imai, et al., *Nature* 403:795 (2000); K. G. Tanner, et al., *Proc. Natl. Acad. Sci. U.S.A.* 97:14178 (2000)), many important biological functions of sirtuins have been revealed, and the NAD-dependent deacetylation mechanism is well understood (S.-i. Imai, et al., *Trends in Pharmacological Sciences* 31:212 (2010); M. C. Haigis, et al., *Annual Review of Pathology: Mechanisms of Disease* 5:253 (2010)). Based on sequence similarity, sirtuins can be grouped into different classes (R. A. Frye, *Biochem. Biophys. Res. Commun.* 273:793 (2000)). Mammals have seven sirtuins, Sirts1-7. Sirts1-3 belong to Class I, Sirt4 belongs to Class II, Sirt5 belongs to Class III, and Sirt6 and Sirt7 belong to Class IV (R. A. Frye, *Biochem. Biophys. Res. Commun.* 273:793 (2000)).

A major obstacle in the study of sirtuin activity is the fact that four of the seven human sirtuins (Sirts4-7) have either very weak or no deacetylase activity (E. Michishita, et al., *Mol. Biol. Cell* 16: 4623 (2005); M. C. Haigis et al., *Cell* 126:941 (2006); A. Schuetz et al., *Structure* 15:377 (2007); G. Liszt, et al., *J. Biol. Chem.* 280:21313 (2005); E. Michishita et al., *Nature* 452:492 (2008)). This poses many difficulties for the study of Sirtuins and development of small molecules that can modulate their activity. For example, it is difficult to develop inhibitors or activators that target Sirts4-7 because no robust activity assay is available. Also, it is hard to tell whether the inhibitors/activators that target Sirt1, Sirt2, and Sirt3 can also target Sirts4-7.

BRIEF SUMMARY OF THE DISCLOSURE

It has been discovered that Sirt5, a mitochondrial Sirtuin, is an efficient demalonylase and desuccinylase. This disclosure presents evidence of new posttranslational modifications of mammalian mitochondrial proteins, namely, malonylation and succinylation of lysine residues. Sirt5 removes glutaryl, malonyl and succinyl groups from lysine residues of mitochondrial proteins, which is believed to reversibly regulate mitochondrial protein activity. The discovery of this robust enzymatic activity has enabled the development of assays to identify Sirt5 modulators. Sirt5-specific modulators can be used to study the biological function of Sirt5 and to target Sirt5 activities in treating human diseases.

BRIEF DESCRIPTION OF THE FIGURES

FIGS. 7A-7D. HPLC purification of O-malony-ADPR (A) and O-succinyl-ADPR (B) and MS confirmation (C and D). The black traces in A and B are the HPLC traces (detected at 260 nm) for Sirt5-catalyzed demalonylation and desuccinylation of the H3K9 acyl peptides. Incubating the peptides with Sirt1 did not generate the same products (grey traces). The O-malonyl-ADPR (C) and O-succinyl-ADPR (D) were further analyzed by MALDI-MS. The formation of O-malonyl-ADPR and O-succinyl-ADPR suggest that the mechanism of Sirt5-catalyzed reactions is the same as the deacetylation mechanism of Class I sirtuins.

DETAILED DESCRIPTION OF THE DISCLOSURE

Figure 1:
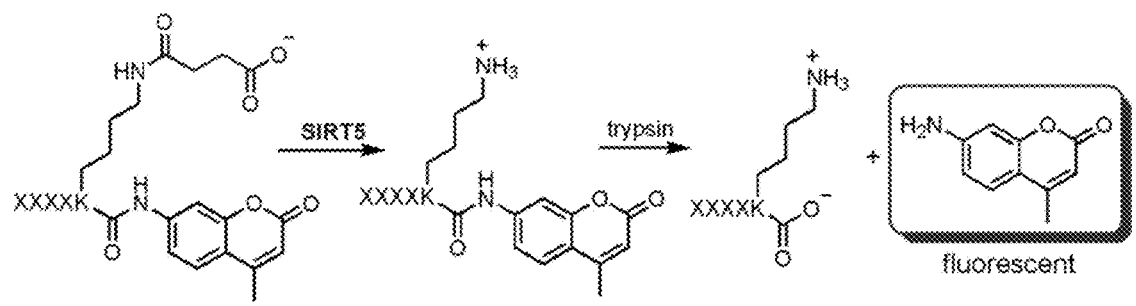
FIG. 1. Fluorogenic assay for Sirt5 using AMC-succinyl peptides.

Sirtuins are a class of evolutionarily conserved enzymes that have been implicated in a wide variety of biological functions. Sirts1-3 are known to have strong deacetylation activity; however, prior to this disclosure, no robust enzymatic activity has been found for Sirts4-7. For example, Sirt5 has poor deacetylation activity, with deacetylase efficiency about 500-fold lower than that of Sirt1.

Sirt5 has been identified herein for the first time to have significantly greater hydrolytic activity with malonyl and succinyl peptides than with acetyl peptides. Further, protein lysine succinylation and malonylation has been shown herein to exist in mammalian cells. In addition, increased levels of lysine succinylation on CPS1, a known Sirt5 target protein, have been observed in Sirt5 knock out (KO) mouse tissues. Therefore, it is believed that the primary activities of Sirt5 in vivo are desuccinylation and demalonylation, rather than deacetylation.

The identification of this robust Sirt5 enzymatic activity by the inventors has permitted the development of assays to identify Sirt5-specific modulators. Sirt5-specific modulators can be used study the biological function of Sirt5 and to target Sirt5 activities in treating human diseases.

Sirt5 Activity

"Sirt5 activities", as used herein, include enzymatic removal of acyl groups (malonyl, succinyl, glutaryl, and acetyl) from lysine residues. Thus, Sirt5 activities include demalonylation, desuccinylation, deglutarylation, and deacetylation of lysine residues.

In some embodiments, this disclosure is directed to the desuccinylase and demalonylase activities of Sirt5, which have been uniquely identified herein. "Sirt5 desuccinylase activity" refers to Sirt5 enzymatic removal of a succinyl group from a lysine residue. "Sirt5 demalonylase activity" refers to Sirt5 enzymatic removal of a malonyl group from a lysine residue.

Sirt5 can act on a stand-alone lysine residue with an acyl group, or on an acylated lysine residue in a peptide or protein. Sirt5 activities, for example, the desuccinylase and demalonylase activities, can occur in vivo as a posttranslational modification of proteins containing succinylated or malonylated lysines, resulting in the generation of downstream physiological events.

A "Sirt5 regulator" or "Sirt5 modulator" or "Sirt5 modulating compound" is a substance that can either activate or inhibit Sirt5 activity. A "Sirt5 inhibitor" is a substance that can reduce or prevent Sirt5 activity. A "Sirt5 activator" is a substance that can enhance or accelerate Sirt5 activity.

Assays for Detecting Sirt5 Activity

In one aspect, this disclosure is directed to an assay for determining the level of Sirt5 demalonylase, desuccinylase or deglutarylase activity in a sample.

The assay is based on the use of a substrate containing a malonyl, succinyl or glutaryl lysine, linked to an indicator moiety. The linkage between the lysine and the indicator moiety can be severed by a cleavage agent which is sensitive to the state of malonylation, succinylation or glutarylation of the lysine residue. Thus, when the substrate is contacted with Sirt5 under conditions for Sirt5 to demalonylate, desuccinylate or deglutarylate the substrate, the removal of the acyl group (possibly leading to the exposure of the cleavage site) permits the cleavage agent to act on the cleavage site and releases the indicator moiety, which then generates a detectable signal.

Substrates suitable for use in the assay for assessing Sirt5 activity can be any molecule containing a succinylated, malonylated or glutarylated lysine residue, including a stand-alone lysine residue as well as peptides containing a lysine. In specific embodiments, the substrate used in the assay is a peptide containing a succinylated or malonylated lysine residue, linked to an indicator moiety.

As used herein, the term "peptide" includes two or more amino acids linked by peptide bonds. There is no particular limitation on the chain length of the peptide. The peptide chain can be as short as 4 or 5 amino acids, and can be as long as 50 amino acids or longer. In some embodiments, the peptide utilized in an assay is 15-25 amino acids in length. There is also no particular limitation on the amino acid sequence of the peptide, except that the peptide includes a succinylated, malonylated or glutarylated lysine, generally at the C-terminus of the peptide. Preferably, the peptide substrate does not have an arginine or lysine residue before the succinyl or malonyl lysine residue, so that the linkage between the succinyl or malonyl lysine and the indicator moiety (such as an amide bond) can be efficiently acted on by a cleavage agent once the succinyl or malonyl group is removed. In a specific embodiment, the peptide chain has the sequence, isoleucine-serine-glycine-alanine-serine-glutamate-lysine (ISGASEK, SEQ ID NO: 1), wherein the lysine is acylated (succinylated, malonylated or glutarylated).

The malonyl, succinyl or glutaryl lysine, whether standalone or as part of a peptide, is linked to an indicator moiety. The linkage is a covalent link which can be severed by a cleavage agent after the acyl group on the lysine is removed. For example, the covalent link is an amide bond formed between the carboxyl group of the malonyl, succinyl or glutaryl lysine and an amino group of an indicator compound, which is susceptible to cleavage by a proteolytic enzyme after the acyl group on the lysine is removed (resulting in the exposure of the peptide bond to the proteolytic enzyme, for example).

The cleavage agent can be any agent which is capable of predictably cleaving peptides between specific amino acid residues (i.e., the proteolytic cleavage pattern), but is incapable of cleaving the peptide bonds if the lysine is succinylated, malonylated or glutarylated. According to one embodiment, a cleavage agent is a proteolytic enzyme, i.e., an enzyme that hydrolyzes a peptide bond (also referred to as peptidase). Examples of proteolytic enzymes include but are not limited to trypsin, calpain, lysylendopeptidase, endoproteinase Lys-C, metalloendopeptidase, plasmin, carboxypeptidase, chymotrypsin, V8 protease, pepsin, papain, subtilisin, thrombin, elastase, gluc-C, endo lys-C or proteinase K, caspase-1, caspase-2, caspase-3, caspase-4, caspase-5, caspase-6, caspase-7, caspase-8, MetAP-2, adenovirus protease, HIV protease and the like.

In a specific embodiment, the cleavage agent is trypsin. Trypsin hydrolyzes peptide bonds whose carbonyl groups are contributed by lysine and arginine residues; thus, trypsin will cleave peptides attached to the carboxy terminus of the lysine residue of the Sirt5 substrate. Another suitable cleavage agent is pepsin, which hydrolyzes peptide bonds on the amino termini of phenylalanine, tryptophan, and tyrosine residues; thus, pepsin will cleave a substrate peptide between a lysine residue and an adjacent phenylalanine, tryptophan, or tyrosine residue.

In these assays, Sirt5 enzymatic activity followed by proteolytic digestion with a cleavage agent separates the indicator moiety from the peptide, generating a detectable signal.

An "indicator moiety" is a molecule or component of the Sirt5 substrate that enables detection of Sirt5 activity. An indicator moiety may be, for example, a fluorescent or other tag molecule, such as 7-amino-4-methylcoumarin (AMC), FLAG, or his-tag. In specific embodiments, the indicator moiety has fluorescent properties.

In one embodiment, the indicator moiety is a single fluorescent small molecule or fluorophore. A "fluorophore" is a component of a molecule that causes a molecule to be fluorescent. It is a functional group in a molecule that will absorb energy of a specific wavelength and re-emit energy at a specific wavelength. Common fluorophores are fluorescein isothiocyanate (FITC), derivatives of rhodamine (TRITC), coumarin, pyrene, cyanine, maleimide derivative dyes, CF dyes, the FluoProbes dyes, the DyLight Fluors, the Oyester dyes, the Atto dyes, the HiLyte Fluors, luciferins, and the Alexa Fluors. Luciferins, such as firefly luciferin, can emit light when incubated with firefly luciferase and ATP. The light emitted can be used to detect Sirt5 activity.

In some embodiments, the fluorophores used in the assays herein are such that changes in fluorescence intensity or emission wavelength depending on the presence or absence of a linkage between the fluorophore and the peptide, and the changes in the fluorescence intensity or emission wavelength can be measured with a fluorescence spectrophotometer. In one embodiment, the indicator moiety is an aminomethylcoumarin moiety. In a specific embodiment, the indicator moiety is 7-amino-4-methylcoumarin (AMC). Thus, a specific example of a fluorogenic substrate for Sirt5 desuccinylase activity is an AMC-succinyl peptide, such as ISGASE(SuK)-AMC (where SuK stands for succinyl lysine), a peptide sequence derived from glutamate dehydrogenase. Similarly, an example of a fluorogenic substrate for Sirt5 demalonylase activity is an AMC-malonyl peptide, such as ISGASE(MaK)-AMC (where MaK stands for malonyl lysine).

In other embodiments, the fluorophore attached to the acylated lysine does not necessarily change in fluorescence intensity or emission wavelength depending on the presence or absence of a linkage between the fluorophore and the peptide; however, the substrate peptide is also labeled with a quenching group. For example, the fluorophore can be attached to the carboxyl terminus of an acylated lysine peptide, while the quenching group can be attached to a different amino acid in the peptide chain containing the acylated lysine. The fluorescence intensity of these substrates is low due to the existence of a quenching group within the substrate. However, the fluorescence intensity is enhanced when the peptide is cleaved on the C-terminal side of the lysine residue by a cleavage agent. This allows measurement of the quantity of the cleaved substrate peptide. Examples of quenching groups suitable for use herein include DNP, Black Hole Quencher™ moieties, and DABCYL.

In another embodiment, the indicator moiety is a fluorescent small molecule or fluorophore which is a member of a donor-acceptor pair of fluorescent molecules. In this embodiment, the indicator fluorophore is linked to the carboxyl terminal of the acyl lysine peptide (typically in this "FRET" embodiment the peptide includes one or more amino acids at the C-terminal side of the acyl lysine), while the other member of the donor-acceptor pair is placed in proximity, e.g., attached to another amino acid of the peptide substrate. Thus, prior to the cleavage of the link between the lysine and the indicator moiety, the donor and receptor fluorophores are in proximity for energy transfer from the donor and acceptor, where such energy transfer can be measured by FRET. Fluorescence Resonance Energy Transfer (FRET) is a non-radiative pathway by which a molecule in an electronic excited state may relax back to the more stable ground state. The transfer of energy occurs through space via dipole-dipole interaction: energy from the excited-state molecule (the donor fluorophore) transfers to a neighboring molecule (the acceptor fluorophore) given the appropriate distance between the two fluorophores. In this embodiment, Sirt5 activity followed by proteolytic cleavage leads to the release of one fluorophore of the pair from the substrate and separates the fluorophores, reducing FRET signal intensity, which can be correlated with Sirt5 activity.

To perform an assay for detecting Sirt5 activity, a sample containing Sirt5 is first brought into contact with a suitable substrate described herein and incubated under appropriate conditions. By "sample" it refers to any sample of interest which contains purified, partially purified, or unpurified Sirt5, and can be a lysate from cells or tissues, or a preparation of Sirt5 protein (purified from cells or tissues or a recombinant expression system). Following the incubation period between a Sirt5 sample and a substrate, a cleavage agent is added to the reaction along with an appropriate reaction buffer. Following this second incubation period, the reaction can be diluted with water or other neutral-pH buffer, and fluorescence is recorded by a fluorescence detector that detects fluorescence at appropriate excitation and detection wavelengths for the fluorophore used. The signal intensity is then correlated with Sirt5 activity.

The assays can be performed in a microplate format. For example, a substrate peptide is added to a reaction buffer, and the solution is poured into the wells of a microplate for fluorometry and the plate is incubated. Next, an aliquot of a Sirt5 sample is added to each well, and subjected to deacylation for a given length of time. Subsequently, an aliquot of proteolytic enzyme and an appropriate reaction buffer is added to each well, and then the fluorescence intensity of the solution is measured periodically, using a fluorescence microplate reader.

In some embodiments, to avoid shortage of the substrate peptide relative to the predicted Sirt5 enzyme activity, an excess amount of the substrate peptide is used in the assay. Specifically, in order to determine the Sirt5 activity in a general biological sample, such as cell nuclear extract, the concentration of the substrate to be used in the reaction is typically 1 to 200 µM, and preferably 20 to 50 µM. On the other hand, the concentration of the cleavage agent can be adjusted mainly depending on the quantity of the used substrate peptide. Typically, the amount of the cleavage agent is adjusted according to the predicted quantity of the generated substrate peptide so as to realize enough cleavage of the substrate peptide under a given condition. Preferably, a cleavage agent activity that realizes, for example, even when all the used substrate peptides are deacylated and thus can be cleaved by the cleavage agent, sufficient cleavage of the peptide under a given assay condition is included in the reaction. Specifically, when substrate peptide at a concentration of about 0.01 to 1 mM is used in the reaction, the quantity of trypsin to be used is, for example, typically 0.2 to 5 µg per 60 µl reaction, preferably 1 to 2 µg per 60 µl reaction.

With respect to the first reaction (deacylation by Sirt5), the pH for the reaction can be selected by taking the optimal pH of Sirt5 into consideration. For example, the pH is typically adjusted to pH 6.0 to 8.5, preferably to pH 6.8 to 8.5. The reaction buffer can be selected from those giving the above-mentioned pH. For example, Tris-HCl, Hepes-KOH, and so on can be used in the method of the present invention. More specifically, for example, 20 mM Tris-HCl, pH 7.4 can be used. NAD is the co-substrate required for Sirt5 and is typically used at 0.5 mM concentration. It is preferable to add salts, and preservatives, in the reaction solution. For example, 1 mM dithiothreitol (DTT) can be added to the reaction. The first reaction (deacylation by Sirt5) can be incubated between 2-20 hours at 35-40° C. Specific exemplary incubation conditions include, for example, incubating a liquid mixture of a substrate and Sirt5-containing sample in Tris-HCl buffer (pH 7.4, 20 mM) containing NAD (0.5 mM) and DTT (1 mM) for 4 hours at 37° C.

For the second reaction by a cleavage agent, the cleavage agent is added to the reaction along with an appropriate reaction buffer. For example, trypsin (1 µg) and $CaCl_2$ (1 mM) is added and the reaction is incubated for approximately 3 hours at 37° C.

Following trypsin incubation, the reaction can be diluted with water or other neutral-pH buffer, and fluorescence is recorded by a fluorescence detector that detects fluorescence at appropriate excitation and detection wavelengths for the fluorophore used. The signal intensity is then correlated with Sirt5 activity.

Assays for Screening for Sirt5 Modulators

In another aspect, this disclosure is directed to an assay for screening for modulators of Sirt5 demalonylase, desuccinylase or deglutarylase activity.

The screening assay is principally based on the assays for assessing Sirt5 activity described hereinabove, except that the assays are performed in the presence and in the absence of a candidate compound.

A candidate compound is identified as a Sirt5 inhibitor when there is a decrease in Sirt5 demalonylase or desuccinylase activity in the presence of the candidate compound, relative to Sirt5 demalonylase or desuccinylase activity in the absence of the candidate compound. A candidate compound is identified as a Sirt5 activator when there is an increase in Sirt5 demalonylase or desuccinylase activity in the presence of the candidate compound, relative to Sirt5 demalonylase or desuccinylase activity in the absence of the candidate compound.

Test compounds to be used in this screening method include, for example, synthetic or recombinant peptides; low-molecular-weight synthetic compounds (small molecules); cell extracts derived from animals, plants or bacteria; cell culture supernatants.

Coupling Demalonlylase/Desuccinylase Assays with Deacetylase Assay for Specificity The assays for screening for Sirt5 modulators described above can include an additional, secondary assay step for deacetylase activity, to identify compounds that modulate Sirt5 but do not modulate Sirts1-3 or other sirtuins that have deacetylase activity. In this secondary assay, an AMC-acetyl peptide is used, for example, to test a compound, identified as a Sirt5 regulator, for ability to modulate Sirts1/2/3. In a specific example, the AMC-acetyl peptide is ISGASE (AcK)-AMC peptide, where AcK is acetyl lysine. A compound identified as a Sirt5 regulator is subject to further testing using the substrate ISGASE(AcK)-AMC and any of Sirts1-3. In this secondary assay, a compound that is found to modulate Sirt5 activity and also modulates activity of any of Sirts1-3 is not considered Sirt5-specific modulator. However, a compound that is found to modulate Sirt5 activity but does not modulate activity of any of Sirts1-3 is identified as a Sirt5-specific modulator. Thus, a Sirt5 assay with, for example, an AMC-succinyl peptide, coupled with a Sirt1/2/3 assay with AMC-acetyl peptide, can be used to screen for compounds that selectively modulate Sirt5 activity.

All assays can be miniaturized and automated for high-throughput analysis. The assays can be performed in one or more separate containers; however, one of the benefits of the disclosed assays is the ability of the assays to be carried out in a single container, such as a microplate well, which allows for ease of use and automation. The substrate may optionally be immobilized on a solid material, such as by biotin-streptavidin linkage, in situations where such immobilization is desired.

Methods to synthesize the substrates described herein are known in the art. For example, synthesis of substrates for use in the fluorogenic assay disclosed above is described in the Examples that follow.

Additional Assay Formats

Another assay provided herein is a mass spectrometry assay. In this assay, Sirt5 activity is identified by determining of the mass of the substrate peptide following contact with Sirt5. Comparison of the amount of starting material (i.e., succinylated, malonylated, or glutarylated peptide) to product (i.e., desuccinylated, demalonylated, or deglutarylated peptide) correlates with the amount of Sirt5 activity on the substrate. In this assay, an increase in product indicates Sirt5 activity, and little or no product indicates little or no Sirt5 activity.

Using a mass spectrometry assay, a candidate compound can be identified as a Sirt5 inhibitor or a Sirt5 activator as follows. A candidate compound is identified as a Sirt5 inhibitor when there is a decrease in product (i.e., desuccinylated, demalonylated, or deglutarylated peptide) produced in the presence of the candidate compound, relative to product produced in the absence of the candidate compound. A candidate compound is identified as a Sirt5 activator when there is an increase in product (i.e., desuccinylated, demalonylated, or deglutarylated peptide) produced in the presence of the candidate compound, relative to product produced in the absence of the candidate compound. The difference in activity between the presence and absence of a modulating compound should be at least 20%, 30%, 40%, 50%, 60%, 70%, 80%, 90%, 100%, 200%, 300%, 400%, 500% or greater.

$IC_{50}$ and $EC_{50}$

The ability of a candidate compound to inhibit Sirt5 activity is measured by determining the $IC_{50}$ of the candidate compound. The ability of a candidate compound to activate Sirt5 activity is measured by determining the $EC_{50}$ of the candidate compound. As used herein, "$IC_{50}$" or "half maximal inhibitory concentration" identifies how much of a compound is needed to inhibit activity by half. The $IC_{50}$ of a compound can be determined by constructing a dose-response curve and examining the effect of different concentrations of a compound on reducing or preventing enzymatic activity. $IC_{50}$ values can be calculated for a given inhibitor by determining the concentration needed to inhibit half of the maximum enzymatic activity. Such concentration measures typically follow a sigmoidal curve, increasing rapidly over a relatively small change in concentration. The point at which the effectiveness slows with increasing concentration is the $IC_{50}$. This can be determined mathematically by derivation of the best-fit line, as known in the art.

As further used herein, "$EC_{50}$" or "half maximal effective concentration" refers to the concentration of a compound which induces a response halfway between the baseline and maximum. The $EC_{50}$ of a graded dose-response curve therefore represents the concentration of a compound where 50% of its maximal effect is observed.

The Sirt5 inhibitors of the invention preferably inhibit Sirt5 activity with an $IC_{50}$ less than or equal to 5 µM. Even more preferably, the Sirt5 inhibitors inhibit Sirt5 demalonylase and desuccinylase activity with an $IC_{50}$ less than or equal to 5 µM and inhibit deacetylase activity of Sirts1-3 with an $IC_{50}$ greater than or equal to 100 µM. A candidate compound that inhibits Sirt5 demalonylase and desuccinylase activity with an $IC_{50}$ less than or equal to 5 µM and inhibits deacetylase activity of any of Sirts1-3 with an $IC_{50}$ greater than or equal to 100 µM is considered a Sirt5-specific inhibitor.

The Sirt5 activators of the invention preferably activate Sirt5 activity with an $EC_{50}$ less than or equal to 5 µM. Even more preferably, the Sirt5 activators activate Sirt5 demalonylase and desuccinylase activity with an $EC_{50}$ less than or equal to 5 µM and activate deacetylase activity of Sirts1-3 with an $EC_{50}$ greater than or equal to 100 µM. A candidate compound that activates Sirt5 demalonylase and desuccinylase activity with an $EC_{50}$ less than or equal to 5 µM and activates deacetylase activity of any of Sirts1-3 with an $EC_{50}$ greater than or equal to 100 µM is considered a Sirt5-specific activator.

Kits Useful for Performing the Assays

In another aspect, this disclosure provides kits for measuring the activity of Sirt5 in a sample, and for screening for compounds that inhibit or enhance the Sirt5 activity described above. The kits provided herein contain a substrate peptide which includes an acylated lysine, as described hereinabove.

One embodiment provides a reagent kit for measuring Sirt5 activity, comprising: (a) a substrate peptide; and (b) a cleavage agent whose activity of cleaving the substrate peptide changes upon the changes of the acylation level of the substrate peptide.

Another embodiment provides a reagent kit for screening for compounds that inhibit or enhance Sirt5 activity, comprising: (a) a substrate peptide; (b) Sirt5; and (c) a cleavage agent whose activity of cleaving the substrate peptide changes upon the changes of the acylation level of the substrate peptide. Typically, each component, (a) the substrate peptide, (b) Sirt5, and (c) the cleavage agent is packaged separately.

Respective components of the kit of the present invention are combined so as to realize a final concentration that is suitable for the reaction. Further, in addition to these components, the kit can include buffer that gives a condition suitable for the reaction. The enzyme preparation and the substrate peptide may be combined with other components that stabilize proteins. For example, it is preferable to add BSA to the preparation at a final concentration of about 1% and polyols, such as sucrose and fructose, at a final concentration of 0.2 to 10%, preferably 1% as agents preventing protein denaturation after lyophilization. Each component of the kit according to the present invention can be provided in liquid form or dried form. Detergents, preservatives, buffers, and so on, commonly used in the art may be added to the components so long as they do not inhibit the measurement of the deacylase activity.

Candidate Inhibitors-Synthesis

Thiosuccinyl and thiomalonyl peptides can inhibit Sirt5 desuccinylase and demalonylase activities by forming a stalled covalent intermediate. These thiosuccinyl and thiomalonyl peptides can undergo the first step of the Sirt5-catalyzed reaction, forming a covalent intermediate which cannot proceed further. Because other sirtuins do not recognize malonyl and succinyl lysine peptides, thiomalonyl and thiosuccinyl peptides are Sirt5-specific inhibitors.

In one embodiment, the candidate compound is a small molecule. A "small molecule" refers to small organic compounds, such as heterocycles, peptides, saccharides, steroids, and the like. The small molecule modulators preferably have a molecular weight of less than about 1500 Daltons, 1000 Daltons, 800 Daltons, or even less than about 500 Daltons. The compounds may be modified to enhance, for example, efficacy, stability, or pharmaceutical compatibility. In a specific embodiment, the Sirt5 inhibitor is a H3K9 thiosuccinyl (H3K9 TSu) peptide. Thiosuccinyl is chosen over thiomalonyl because succinyl lysine has a lower $K_m$ value for Sirt5 than malonyl lysine.

Sirt5 Specific Inhibitors

The disclosure provides compounds that inhibit Sirt5 demalonylase or desuccinylase activity. The Sirt5 inhibitors considered herein can be described by the following generic formula:

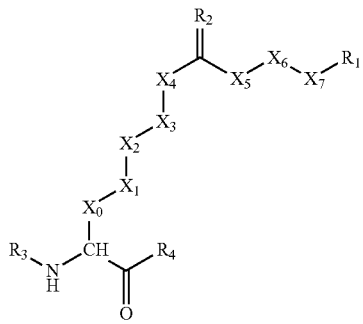

(1)

In Formula (1), $R_1$ is a negatively-charged (i.e., anionic) or ionizable group. Some examples of negatively-charged or ionizable groups include carboxylate (—COO⁻), carboxylic acid (—COOH), thiocarboxylate (—CSO⁻), sulfonate (—SO$_3^-$), phosphonate (—PO$_3^{2-}$), and nitro (—NO$_2$) groups. The group $R_2$ is selected from S, NR$_5$, and O, wherein $R_5$ can be a hydrogen atom (H) or a hydrocarbon group containing one to seven carbon atoms (e.g., methyl, ethyl, isopropyl, phenyl, or benzyl). The groups $X_0$, $X_1$, $X_2$, $X_3$, $X_4$, $X_5$, $X_6$ and $X_7$ are independently selected from —(CH$_2$)$_n$— (wherein n represents 1, 2, or 3), —NR$_5$—, —O—, —S—, or a bond, provided that at least one of $X_0$-$X_4$ is not a bond, and at least one of $X_5$-$X_7$ is not a bond. Generally, $X_5$, $X_6$, and $X_7$ are —CH$_2$— groups or a bond, provided that at least one of $X_5$-$X_7$ is not a bond. Often, at least one, two, three, or all four of $X_0$-$X_3$ are —CH$_2$— groups, while $X_4$ is selected from —CH$_2$—, —NR$_5$—, —O—, or —S— groups. In specific embodiments, all four of $X_0$-$X_3$ are —CH$_2$— groups, while $X_4$ is selected from —CH$_2$—, —NR$_5$—, —O—, or —S— groups, and $X_5$-$X_7$ are —CH$_2$— groups or a bond, provided that at least one of $X_5$-$X_7$ is not a bond. The groups $R_3$ and $R_4$ are independently selected from H, hydrocarbon (R), amino acid, dipeptide, tripeptide, oligopeptide (e.g., from 4, 5, 6, 8, 10, 12, or 15 amino acid residues up to 20, 25, 30, 35, 40, 45, or 50 amino acid residues), protein, nucleobase, nucleotide, dinucleotide, trinucleotide, oligonucleotide, monosaccharide, disaccharide, oligosaccharide, and protecting groups (e.g., tBOC or FMOC groups), or a combination thereof or modified form thereof (e.g., lipoprotein or nucleoprotein), wherein $R_4$ may also be a —OR, —NHR, or —NC(O)R group, and $R_3$ may also be a —C(O)R or —C(O)NHR group. Generally, when $R_1$ is carboxyl, then $R_2$ is not O, and when $R_2$ is O, then $R_1$ is not carboxyl.

In particular embodiments of Formula (1), $R_2$ is S, thus resulting in a sub-generic set of compounds of the following formula:

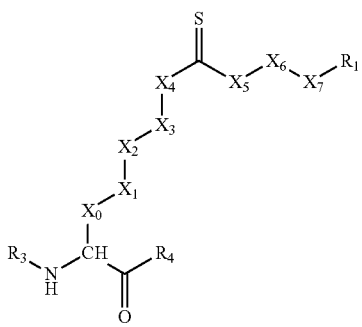

(1a)

In other particular embodiments of Formula (1), $R_2$ is S and $R_1$ is carboxyl, thus resulting in a sub-generic set of compounds of the following formula:

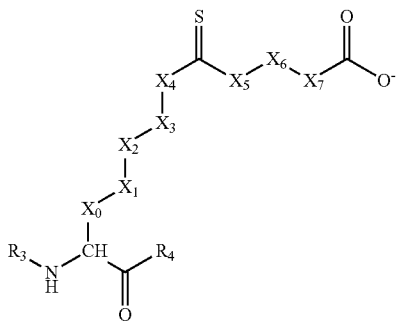

(1b)

In still other particular embodiments of Formula (1), $R_2$ is S, $R_1$ is carboxyl, and $X_4$ is —NR$_5$—, thus resulting in a sub-generic set of compounds of the following formula:

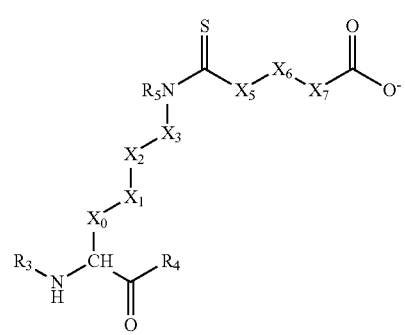

(1c)

In Formula (1c), $X_0$-$X_3$ are preferably selected from —(CH$_2$)$_n$— groups (wherein n represents 1, 2, or 3) or a bond, wherein at least one of $X_0$-$X_3$ is not a bond; and $X_5$-$X_7$ are preferably —CH$_2$— groups or a bond, and at least one of $X_5$-$X_7$ is not a bond. In specific embodiments, all four of $X_0$-$X_3$ are —CH$_2$— groups, and $X_5$-$X_7$ are CH$_2$— groups or a bond provided at least one of $X_5$-$X_7$ is not a bond.

The double-bonded group $R_2$ in Formula (1) may alternatively be replaced with two single-bonded groups ($R_5$ and $R_6$), as shown in the following sub-formula:

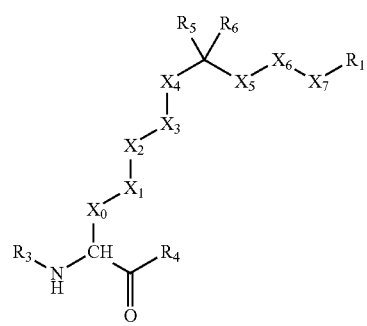

(2)

In Formula (2), $R_5$ and $R_6$ are independently selected from H, a hydrocarbon group (R) having one to six carbon atoms, OH, OR, SH, SR, and NHR, except that, generally, both of $R_5$ and $R_6$ are not selected from OH, OR, SH, SR, and NHR (i.e., if one of $R_5$ and $R_6$ is OH, OR, SH, SR, or NHR, then the other of $R_5$ and $R_6$ is H or R). In some embodiments, when one of $R_5$ and $R_6$ is a OH or OR group, then $R_1$ is not a carboxyl group.

The terms "hydrocarbon group" and "hydrocarbon linker", as used herein, are, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, or eighteen carbon atoms, or a particular range of carbon atoms between any of the foregoing carbon numbers.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene, i.e., —$CH_2$—, or methine linkers), ethyl (or ethylene or dimethylene, i.e., —$CH_2CH_2$— linkers), n-propyl, n-butyl, n-pentyl, and n-hexyl groups.

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, and 3-methylpentyl. Some examples of branched alkylene linkers are those derived by removal of a hydrogen atom from one of the foregoing exemplary branched alkyl groups (e.g., isopropylene, —CH($CH_3$)$CH_2$—).

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, and cycloheptyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, 2-propen-1-yl (allyl), 3-buten-1-yl, 2-buten-1-yl, butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, and propargyl (2-propynyl). Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers can alternatively be unsaturated and branched (i.e., branched olefinic or alkenyl groups or linkers). Some examples of branched olefinic groups include 2-propen-2-yl, 3-buten-2-yl, 3-buten-3-yl, 4-penten-2-yl, 4-penten-3-yl, 3-penten-2-yl, 3-penten-3-yl, and 2,4-pentadien-3-yl. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). Some examples of unsaturated and cyclic hydrocarbon groups include cyclopropenyl, cyclobutenyl, cyclopentenyl, cyclopentadienyl, cyclohexenyl, cyclohexadienyl, phenyl, and benzyl. The unsaturated cyclic hydrocarbon group can also be a polycyclic (e.g., bicyclic) group by either possessing a bond between two of the ring groups (e.g., biphenyl) or a shared (i.e., fused) side (e.g., naphthalene, anthracene, phenanthrene, phenalene, and indene). Some examples of cycloalkenylene linkers are those derived by removal of a hydrogen atom from one of the foregoing exemplary cycloalkenyl groups (e.g., phenylene and biphenylene).

In some embodiments, one or more of the hydrocarbon groups or linkers may also include one or more heteroatoms (i.e., non-carbon and non-hydrogen atoms), such as one or more heteroatoms selected from oxygen, nitrogen, sulfur, halide, and phosphorus atoms. Some examples of oxygen-containing groups include hydroxyl (OH) groups, carbonyl groups (e.g., ketone, aldehyde, ester, amide, or urea functionalities), and carbon-oxygen-carbon (ether) groups. The ether group can also be a polyalkyleneoxide group, such as a polyethyleneoxide group. Some examples of nitrogen-containing groups include primary amine groups, secondary amine groups, tertiary amine groups, quaternary amine groups, cyanide group, amide group (i.e., —C(O)$NR_2$, wherein R is independently selected from hydrogen atom and hydrocarbon group, as described above), nitro group, urea group, imino group, and carbamate group, wherein it is understood that a quaternary amine group necessarily possesses a positive charge and requires a counteranion. Some examples of sulfur-containing groups include mercapto (i.e., —SH), thioether (i.e., sulfide), disulfide, sulfoxide, sulfone, sulfonate, and sulfate groups. Halide atoms considered herein include fluorine, chlorine, and bromine.

In a specific embodiment, the candidate compound is a thiosuccinyl compound. In a preferred embodiment, the candidate compound is H3K9 thiosuccinyl peptide.

The synthesis of the inhibitor compounds described above relies on established and well-known methodologies of the art. For example, the coupling of malonate and succinylate to lysine side chains can be accomplished using well known reaction conditions for the preparation of amides from amines and carboxylic acids. The conversion of a carbonyl oxygen atom (e.g., $R_2$) to a thiocarbonyl can be accomplished by, for example, reaction with Lawens son reagent by methods well known in the art.

Compositions

Any of the Sirt5-modulating compounds described herein can be made or modified to have improved properties for administration to a mammalian subject, e.g., to improve stability, cell penetrating ability, among others. For example, to enhance cell permeability of the substrate, the peptide chain can include a string of multiple amino acids (such as 8-10 arginine residues).

Sirt5-modulating compounds described herein may be formulated in a conventional manner using one or more physiologically acceptable carriers or excipients. For example, Sirt5-modulating compounds and their physiologically acceptable salts and solvates may be formulated for administration by, for example, injection (e.g. SubQ, IM, IP, IV), inhalation or insufflation (either through the mouth or the nose) or oral, buccal, sublingual, transdermal, nasal, parenteral or rectal administration. In one embodiment, a Sirt5-modulating compound may be administered locally, at the site where the target cells are present, i.e., in a specific tissue, organ, or fluid (e.g., blood, cerebrospinal fluid, etc.). Sirt5-modulating compounds can be formulated for a variety of modes of administration, including systemic and topical or localized administration. Techniques and formulations generally may be found in Remington's Pharmaceutical Sciences, Meade Publishing Co., Easton, Pa.

Pharmaceutical compositions (including cosmetic preparations) may comprise from about 0.00001 to 100% such as from 0.001 to 10% or from 0.1% to 5% by weight of one or more Sirt5-modulating compounds described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Toxicity and therapeutic efficacy of Sirt5-modulating compounds can be determined by standard pharmaceutical procedures in cell cultures or experimental animals. The $LD_{50}$ is the dose lethal to 50% of the population. The dose ratio between toxic and therapeutic effects ($LD_{50}/ED_{50}$) is the therapeutic index. Sirt5-modulating compounds that exhibit large therapeutic indexes are preferred. While Sirt5-modulating compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

Methods of Treatment/Conditions Treatable

The disclosure further provides methods to treat or prevent a disorder characterized by abnormal Sirt5 demalonylase or desuccinylase activity. Such methods are based on administering to a subject a Sirt5 modulator in an effective amount to treat or prevent the disorder. In certain aspects, the invention provides methods for modulating the activity of Sirt5 and methods of use thereof.

In certain embodiments, the invention provides methods for using Sirt5 inhibitors or activators. Sirt5 inhibitors may be useful for a variety of therapeutic applications including, for example, increasing the lifespan of a cell, and treating and/or preventing diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a Sirt5 inhibitor.

In certain embodiments, the Sirt5-modulating compounds described herein may be taken alone or in combination with other compounds. In one embodiment, a mixture of two or more Sirt5-modulating compounds may be administered to a subject in need thereof. In another embodiment, one or more Sirt5-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, ageing, stress, etc.

In various embodiments, combination therapies comprising a Sirt5-modulating compound may refer to (1) pharmaceutical compositions that comprise one or more Sirt5-modulating compounds in combination with one or more therapeutic agents (e.g., one or more therapeutic agents described herein); and (2) co-administration of one or more Sirt5-modulating compounds with one or more therapeutic agents wherein the Sirt5-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the Sirt5 modulating compound(s) and other therapeutic agent(s) are in separate vessels). When using separate formulations, the Sirt5-modulating compound may be administered at the same, intermittent, staggered, prior to, subsequent to, or combinations thereof, with the administration of another therapeutic agent.

EXAMPLES

Example 1

Reagents and Instrumentation.

Reagents were obtained from Aldrich or Acros in the highest purity available and used as supplied. $^1$H NMR, $^{13}$C NMR and 2D NMR were performed on INOVA 500 spectrometer. NMR data was analyzed by MestReNova (version 5.2.5). LCMS was carried out on a SHIMADZU LCMS-QP8000α with a Sprite TARGA C18 column (40×2.1 mm, 5 μm, Higgins Analytical, Inc., Mountain View, Calif.) monitoring at 215 and 260 nm. Solvents used in LCMS were water with 0.1% formic acid and acetonitrile with 0.1% formic acid.

Synthesis of Fmoc-Lys(tBu-malonyl)-OH and Fmoc-Lys (tBu-succinyl)-OH.

Mono-tbutyl-malonate (480 mg, 3.0 mmol) or mono-tbutyl-succinate (522.0 mg, 3 mmol) in anhydrous N,—N'-dimethylformamide (DMF, 2.0 mL) was added to N-hydroxysuccinimide (334 mg, 2.9 mmol) with stifling at room temperature. Then N,N'-dicyclohexylcarbodiimide (598 mg, 2.9 mmol) in anhydrous DMF (3.0 mL) was added to the reaction. After stifling for 2 h, the reaction mixture was filtered. The filtrate was added to a solution of Fmoc-Lys-OH (736 mg, 2.0 mmol) with N, N-diisopropylethylamine (DIEA, 1.0 mL, 5.8 mmol) in anhydrous DMF (2.0 mL) at room temperature. The resulting reaction mixture was stirred for another 30 min. Then the reaction mixture was added 10 mL water and 6 mL 1 M HCl to adjust pH to 2~3. The mixture was extracted three times by 100 mL ethyl acetate and washed twice with 50 mL brine. The organic layer was dried with anhydrous sodium sulfate. After removal of the solvents in vacuo, the residue was purified by silica gel column using 10:1 $CH_2Cl_2$:$CH_3OH$ to give the desired product in about 90% yield.

Fmoc-Lys(tBu-Malonyl)-OH. $^1$H NMR (500 MHz, DMSO-d$_6$): δ8.01 (t, 1H, J=5.5 Hz), 7.89 (d, 2H, J=7.0 Hz), 7.73 (dd, 2H, J=2.0, 7.0 Hz), 7.46 (d, 1H, J=7.0 Hz), 7.41 (t, 2H, J=7.5 Hz), 7.33 (t, 2H, J=7.8 Hz), 4.27 (m, 2H), 4.23 (m, 1H), 3.87 (dt, 1H, J=4.5, 8.5 Hz), 3.07 (s, 2H), 3.03 (m, 2H), 1.65 (m, 2H), 1.39 (m, 2H), 1.38 (s, 9H), 1.33 (m, 2H). $^{13}$C NMR (125 MHz, DMSO-d$_6$): δ174.26, 167.29, 165.24, 156.08, 143.91, 143.84, 140.75, 140.73, 127.66, 127.11, 125.33, 120.15, 120.14, 80.40, 80.39, 65.57, 54.10, 46.70, 43.74, 38.51, 30.74, 28.65, 27.70, 23.02. LCMS (ESI) calcd. for C$_{28}$H$_{35}$N$_2$O$_7$ [M+H$^+$]511.3, obsd. 510.8.

Fmoc-Lys(tBu-Succinyl)-OH. $^1$H NMR (500 MHz, CD$_3$OD): δ 7.75 (d, 2H, J=8.0 Hz), 7.61 (dd, 2H, J=4.5, 7.5 Hz), 7.35 (t, 2H, J=7.3 Hz), 7.26 (t, 2H, J=7.3 Hz), 4.30 (m, 2H), 4.15 (t, 1H, J=7.0 Hz), 4.04 (dd, 1H, J=4.5, 8.0 Hz), 3.14 (t, 2H, J=7.0 Hz), 2.49 (t, 2H, J=7.0 Hz), 2.38 (t, 2H, J=7.3 Hz), 1.75 (m, 2H), 1.49 (m, 2H), 1.40 (s, 9H), 1.37 (m, 2H). $^{13}$C NMR (125 MHz, CD$_3$OD): δ 180.22, 174.46, 173.72, 158.64, 145.49, 145.28, 142.69, 142.68, 128.91, 128.29, 126.38, 126.35, 121.07, 81.81, 67.97, 57.11, 48.54, 40.37, 33.23, 31.93, 31.87, 30.17, 28.48, 24.32. LCMS (ESI) calcd. for C$_{29}$H$_{37}$N$_2$O$_7$ [M+H$^+$] 525.3, obsd. 524.8.

Synthesis of Acetyl, Thioacetyl, Malonyl, and Succinyl Peptides

Acetyl, thioacetyl, malonyl and succinyl peptides were synthesized on Fmoc-Wang resin using standard Fmoc/tBu chemistry O-benzotriazol-N,N,N',N'-tetramethyluronium hexafluorophosphate/1-hydroxybenzotriazol (HBTU/HOBt) protocol (Du et al., *Biochemistry* 48: 2878-2890, 2009). Modified lysine was incorporated using Fmoc-Lys(acetyl)-OH, Fmoc-Lys(thioacetyl)-OH (Fatkins et al., *Bioorg. Med. Chem. Lett.* 16: 3651-3656, 2006), Fmoc-Lys(tBu-malonyl)-OH and Fmoc-Lys(tBu-succinyl)-OH. Cleavage from the resin and removal of all protecting groups was done by incubating the resin with trifluoroacetic acid (TFA) containing phenol (5%), thioanisole (5%), ethanedithiol (2.5%), and water (5%) for 2 h. The crude peptides were purified by reverse phase HPLC on BECKMAN COULTER System Gold 125P solvent module & 168 Detector with a TARGA C18 column (250×20 mm, 10 μm, Higgins Analytical, Inc., Mountain View, Calif.) monitoring at 215 nm. Mobile phases used were 0.1% aqueous TFA (solvent A) and 0.1% TFA in acetonitrile (solvent B). Peptides were eluted with a flow rate of 10 mL/min with the following gradient: 0% solvent B for 5 min, then 0% to 25% solvent B over 25 min. The identity and purity of the peptides were verified by LCMS. Table 4 herein lists the synthetic peptides.

Cloning, Expression and Purification of Human Sirtuins

Human Sirts1, 2, 3, 5, and 6 were expressed as previously described (J. Du, et al., *Biochemistry* 48:2878 (2009)). Sirt4 was not included in this study due to difficulties in expression. Human Sirt7 coding sequence was PCR-amplified using primers JT072_SIRT7(1-400) EcoRI5 (5'-AGTCAG-GAATTCATGGCAGCCGGGGGTCT-3') (SEQ ID NO:2) and JT073_Sirt7(1-400)XhoI3 (5'-AGTCAGCTCGAGTTA CGTCACTTTCTTCCTTTTT-3') (SEQ ID NO:3). Amplified product was digested with EcoRI and XhoI. The digested PCR product was purified and ligated into the similarly digested expression vector pET28a. C-terminal Flag-tagged Sirt5 (Flag-Sirt5) and truncated Sirt5(34-302) were cloned using TOPO and GATEWAY cloning technology (Invitrogen Corp., Carlsbad, Calif.) into pDEST-F1 for expression. Sirt7, Flag-Sirt5 and Sirt5(34-302) were expressed in *E. coli* and purified as described (J. Du, et al., *Biochemistry* 48:2878 (2009)). After purification, Flag-Sirt5 and Sirt5(34-302) were digested by TEV at room temperature for 2 h and purified by HiTrap™ HP Column (GE Healthcare, Piscataway, N.J.) and gel filtration on a HiLoad 26/60 Superdex 75 prep grade column (GE Healthcare, Piscataway, N.J.). Protein concentrations were determined by Bradford reagent.

Sirt5 X-ray Diffraction Data Collection and Structural Refinement.

Sirt5-H3K9 thioacetyl peptide and Sirt5-H3K9 succinyl peptide were prepared at a 1:20 protein:peptide molar ratio and incubated for 30~60 min on ice. Crystals were grown by the method of hanging drop vapor diffusion. Sirt5-H3K9 succinyl peptide co-crystals were soaked in 10 mM NAD for 10~120 min before data collection. All the X-ray diffraction data were collected at CHESS (Cornell High Energy Synchrotron Source) A1 or F1 station. The data were processed using the programs HKL2000 (Z. Otwinowski, et al., *Methods Enzymol.* 276:472 (1997)). The two structures of Sirt5 complexes were solved by molecular replacement using the program Molrep from the CCP4 suite of programs (Collaborative, *Acta Crystallogr. D Biol. Crystallogr.* 50:760 (1994)). The Sirt5-ADPR structure (PDB code: 2B4Y) was served as the searching template. Refinement and model building were performed with REFMAC5 and COOT from CCP4.

Results. Structure of Sirt5 Reveals an Unusual Acyl Pocket

One possible explanation for the lack of robust deacetylase activity for Sirts4-7 is that they have strict requirement for the peptide sequence. To test this, the activities of six human Sirtuins (all except Sirt4, which could not be expressed in soluble forms in *E. coli*) were monitored using 16 different acetyl peptides. Under the experimental conditions used, Sirt1-3 and 5 showed deacetylase activity, but Sirt6 and Sirt7 did not. All 16 peptides were deacetylated efficiently by Sirt1-3, while only eight were deacetylated slowly by Sirt5. A histone H3K9 acetyl peptide was one of the best substrates for Sirt1-3 and Sirt5. With this peptide, the $k_{cat}$ and $K_m$ of different Sirtuins were determined (Table 1). The catalytic efficiency ($k_{cat}/K_m$) of Sirt5 is about 500-fold lower than that of Sirt1.

TABLE 1

The kinetic parameters of four human sirtuins on H3 K9 acetyl peptide

| Sirtuins | $k_{cat}$ (s$^{-1}$) | $K_m$ for acetyl peptide (μM) | $k_{cat}/K_m$ (s$^{-1}$M$^{-1}$) |
|---|---|---|---|
| Sirt1 | 0.039 ± 0.001 | 38 ± 4 | 1.0 × 10$^3$ |
| Sirt2 | 0.030 ± 0.001 | 190 ± 14 | 1.6 × 10$^2$ |
| Sirt3 | 0.012 ± 0.001 | 50 ± 9 | 2.4 × 10$^2$ |
| Sirt5 | ND* | ND (>750)* | 2.0 |

*The $k_{cat}$ and $K_m$ values for Sirt5 cannot be determined because the V versus [S] plot is linear ($K_m$ is much greater than the highest substrate concentration tested). Thus only $k_{cat}/K_m$ value can be obtained. The $k_{cat}$ and $K_m$ values were obtained by curve-fitting the $V_{initial}/[E]$ versus [S] plot using KaleidaGraph.

Figures 2A, 2B, 2C, 2D:
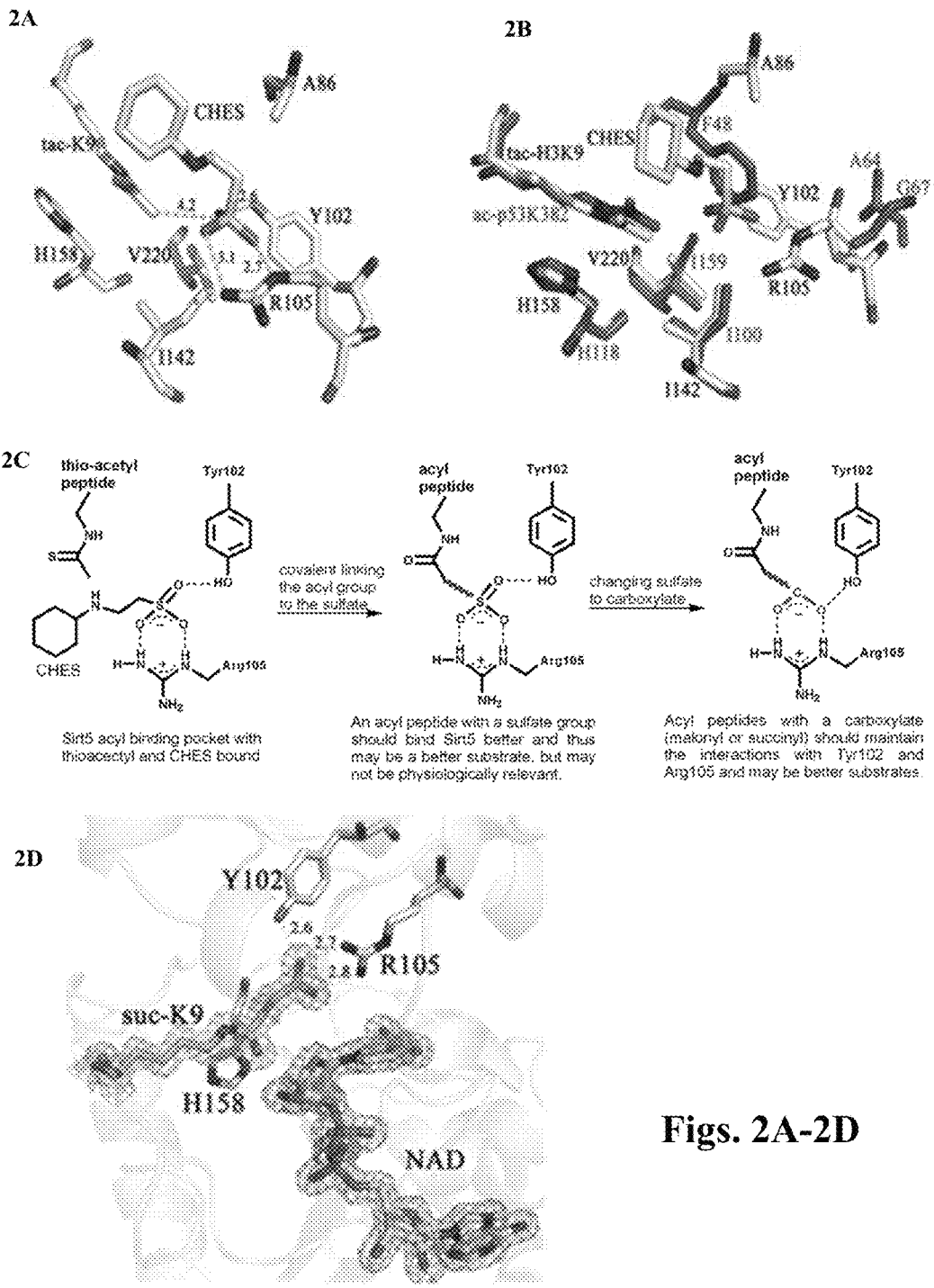
FIGS. 2A-2D. The structure of Sirt5 reveals an unusual acyl pocket. (A) The acyl pocket of Sirt5 is partially occupied by the sulfate from the buffer molecule CHES via interactions with Arg105 and Tyr102. The sulfur is 4.2 Å away from the thioacetyl group. (B) Alignment of Sirt5-thioacetyl peptide structure and Sir2Tm-acetyl peptide structure. (C) The rationale for predicting that malonyl/succinyl peptides may be better substrates for Sirt5. (D) Sirt5-succinyl peptide-NAD ternary structure showing that the succinyl group interacts with Tyr102 and Arg105.

To understand why the deacetylase activity of Sirt5 is weak, crystals of Sirt5 in complex with a thioacetyl peptide were obtained (the corresponding acetyl peptide could not be crystallized with Sirt5). The structure was solved with molecular replacement using reported Sirt5 structures (A. Schuetz et al., *Structure* 15:377 (2007)). In addition to the thioacetyl peptide, a buffer molecule, CHES (N-cyclohexyl-2-aminoethanesulfonic acid), was also bound to Sirt5 (FIG. 2A). The interactions between the thioacetyl peptide and Sirt5 involve mostly backbone hydrogen-bonding interactions, similar to what was observed for *Thermotoga maritime* Sir2 (Sir2Tm), a bacterial Sirtuin with robust deacetylase activity (M. S. Cosgrove et al., *Biochemistry* 45:7511 (2006)). Thus, the selectivity for peptide sequences is unlikely to be the major reason for the lack of robust deacetylase activity for Sirt5.

However, a surprising feature was discovered when the Sirt5 structure was superimposed with the structure of Sir2Tm in complex with an acetyl peptide and NAD (PDB 2h4f) (K. G. Hoff, et al., *Structure* 14:1231 (2006)) (FIG.

2B). The positions of the thioacetyl lysine in Sirt5 and the acetyl lysine in Sir2Tm are almost identical in the superimposed structures. The acetyl group in the Sir2Tm structure is surrounded by three hydrophobic residues, Phe48, Ile100, and Ile159. In contrast, the corresponding pocket in Sirt5 is larger due to the replacement of Phe48 (Sir2Tm number) by Ala86 in Sirt5. Furthermore, the pocket in Sirt5 is bound by the CHES buffer molecule. The sulfate group of CHES interacts with Tyr102 and Arg105 of Sirt5 and is only ~4 Å away from the thioacetyl group (FIG. 2A). In the reported Sirt5 structure with HEPES bound (A. Schuetz et al., *Structure* 15:377 (2007)), the sulfate from HEPES also interacts with Arg105 and Tyr102.

Example 2

Deacetylation, Demaionylation, and Desuccinylation Activity Assay and Determination of $k_{cat}$ and $K_m$.

The deacylase activity of human Sirt1, Sirt2, Sirt3, Sirt5, Sirt6 and Sirt7 were measured by detecting the deacylated peptide from the acyl peptides using LCMS. Purified Sirtuin was incubated with 0.3 mM acyl peptides, 1.0 mM NAD in 20 mM Tris-HCl buffer (pH 7.5) containing 1 mM DTT in 60 µL reactions for 2 h at 37° C. The reactions were stopped with 60 µL 10% TFA and analyzed by LCMS.

For determination of $k_{cat}$ and $K_m$, human Sirt1, Sirt2, Sirt3 and Sirt5 were measured by detecting the deacylated peptide from H3K9 acyl peptides using HPLC. Purified Sirtuin was incubated with 1.0 mM of NAD in 20 mM Tris-HCl buffer (pH 7.5) containing acyl peptides (0-750 µM) and 1 mM DTT in 60 µL reactions at 37° C. The reactions were stopped with 100 mM HCl and 160 mM acetic acid, analyzed by HPLC with a reverse phase C18 column (250×4.6 mm, 90 A, 10 µm, GraceVydac, Southborough, Mass.), with a linear gradient of 0% to 20% B for 10 min (1 mL/min). Product quantification was based on the area of absorption monitored at 215 nm, assuming hydrolysis of the acyl group does not affect the absorption. The $k_{cat}$ and $K_m$ values were obtained by curve-fitting the $V_{initial}$/[E] versus [S] plot using KaleidaGraph. For Sirt5 R105M, the observed second order rate constant, $k_{obs}$ (rate/([Sirtuin][NAD])) was detected instead of $k_{cat}$ and $K_m$ because of the very weak deacylation activity. The experiments were done in duplicate.

For comparing the deacetylation, demalonylation and desuccinylation activities of Sirt5 on different peptide backbones (results shown in Table 2), histone H3, GDH and ACS2 peptides with two tryptophan residues at the C-terminal were used to allow better detection and quantification on HPLC. The determination of $k_{cat}$ and $K_m$ was carried out essentially the same as mentioned above with slight modifications. The reactions were quenched with 60 µL 10% TFA. The chromatography gradient was 0% to 50% B for 20 min (1 mL/min). The peptides were detected and quantified on the LC by the absorption at 280 nm.

Purification of O-Ma-ADPR and O-Su-ADPR with HPLC and Analysis by MS.

Sirt5 or Sirt1 (1 µM) was incubated with 0.5 mM malonyl or succinyl peptides and 1.0 mM NAD in 20 mM Tris-HCl buffer (pH 7.5) with 1 mM DTT in 60 µL reactions for 2 h at 37° C. The reactions were terminated by adding 60 µL 10% TFA. After centrifugation to remove precipitated proteins, the supernatant was analyzed by HPLC using a 50 mM ammonium acetate isocratic system on a Sprite TARGA C18 column (40×2.1 mm, 5 Higgins Analytical, Inc.). The product O-Ma-ADPR (retention time 1.6 min) and O-Su-ADPR (retention time 2.3 min) was collected and the molecular weights were confirmed by MALDI-MS (FIG. 7). The ADPR (retention time 1.2 min) and NAD (retention time 5 min) have also been confirmed by MALDI-MS.

O-Su-ADPR generated from bovine liver mitochondrial peptide mixtures were purified as above and analyzed using an Agilent 1100 high-performance liquid chromatographer coupled to an ABI 4000 Q-trap mass spectrometer operating in IDA negative ion mode. Chromatography consisted of an HILIC column (Nest Group, 100 Å, 5 µm, polyhydroxyethyl A, 1×150 mm) eluted with a gradient of A (acetonitrile) versus B (10 mM ammonium acetate) at 0.05 ml/min. This extra LC step was needed because the sample was more complicated than the reactions using only synthetic peptides.

Results. Sirt5 Prefers to Hydrolyze Malonyl and Succinyl Peptides

Based on the above structural analysis, it appeared that if the acetyl group is replaced with an acyl group bearing a negatively-charged carboxylate, the acyl peptide should bind Sirt5 better than the acetyl peptide and thus may be a better substrate for Sirt5 (FIG. 2C). In cells, the most common acyl-CoA molecules with a carboxylate group are malonyl-CoA and succinyl-CoA. Malonyl-CoA, made from acetyl-CoA by acetyl-CoA carboxylase (ACC), is a precursor for fatty acid biosynthesis (K.-H. Kim, *Ann. Rev. Nutr.* 17:77 (1997); D. Saggerson, *Ann. Rev. Nutr.* 28:253 (2008)). Mammals have two ACC enzymes, ACC1 in the cytosol and ACC2 in the mitochondria (K.-H. Kim, *Ann. Rev. Nutr.* 17:77 (1997)). Succinyl-CoA is an intermediate in the Kreb cycle, which occurs in the mitochondria. Given that acetyl-CoA is used to modify proteins in cells, it is possible that malonyl- and succinyl-CoA can also be used to modify proteins. Thus H3K9 malonyl and succinyl peptides were synthesized and tested for hydrolysis by Sirt5.

Figure 3:
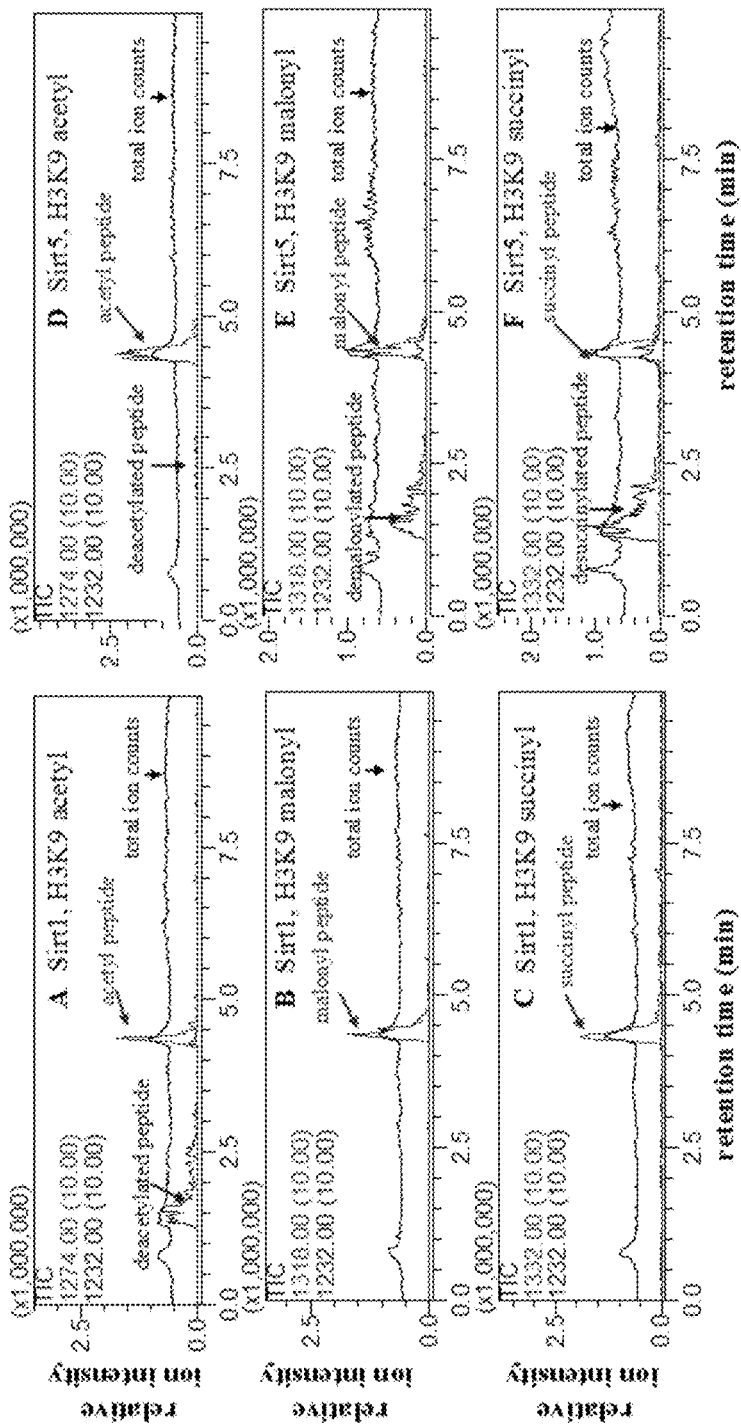
FIGS. 3A-3F. Sirt5 catalyzes the hydrolysis of malonyl and succinyl lysine. Purified Sirtuin (Sirt1 0.75 µM or Sirt5 3.3 µM) was incubated with 0.3 mM acyl peptides, 1.0 mM NAD in 20 mM Tris-HCl buffer (pH 7.5) containing 1 mM DTT in 60 µL reactions for 2 h at 37° C. The reactions were stopped with 60 µL 10% TFA. After removing the precipitated protein, reaction mixture was then analyzed by LCMS. Grey traces show the ion intensities (10× magnified) for the masses of the acyl peptides (acetyl peptide, m/z 1274.0; malonyl peptide, m/z 1318.0; succinyl peptide, m/z 1332.0) and ion intensities (10× magnified) for the mass of the deacylated peptide (m/z 1232.0). Black traces show the ion intensity for all masses from 100-2000 (total ion counts or TIC). With Sirt1, the deacylated product was detected when H3K9 acetyl peptide (A) was used as the substrate and no hydrolysis products were detected using H3K9 malonyl (B) and succinyl (C) peptides. With Sirt5, the deacetylated product was barely detectable (D) while the demalonylated (E) and desuccinylated (F) products were detected.

LC-MS was used to monitor the reactions. Sirt1, which has efficient deacetylase activity, was used as a control. Sirt1 catalyzed the hydrolysis of the acetyl peptide, but not the malonyl and succinyl peptides (FIGS. 3A-C and 5A-C). Similar results were obtained with Sirt2 and Sirt3. In contrast, with Sirt5, very little hydrolysis of the acetyl peptide was observed, but the malonyl and succinyl peptides were hydrolyzed significantly (FIG. 3D-F). The demalonylated/desuccinylated peptides have identical masses with the synthetic unmodified H3 K9 peptide. Sirt6 and Sirt7 have no detectable activity on acetyl, malonyl, or succinyl peptides under the conditions tested. Thus, Sirt5 is an NAD-dependent desuccinylase and demalonylase.

Figures 6A, 6B:
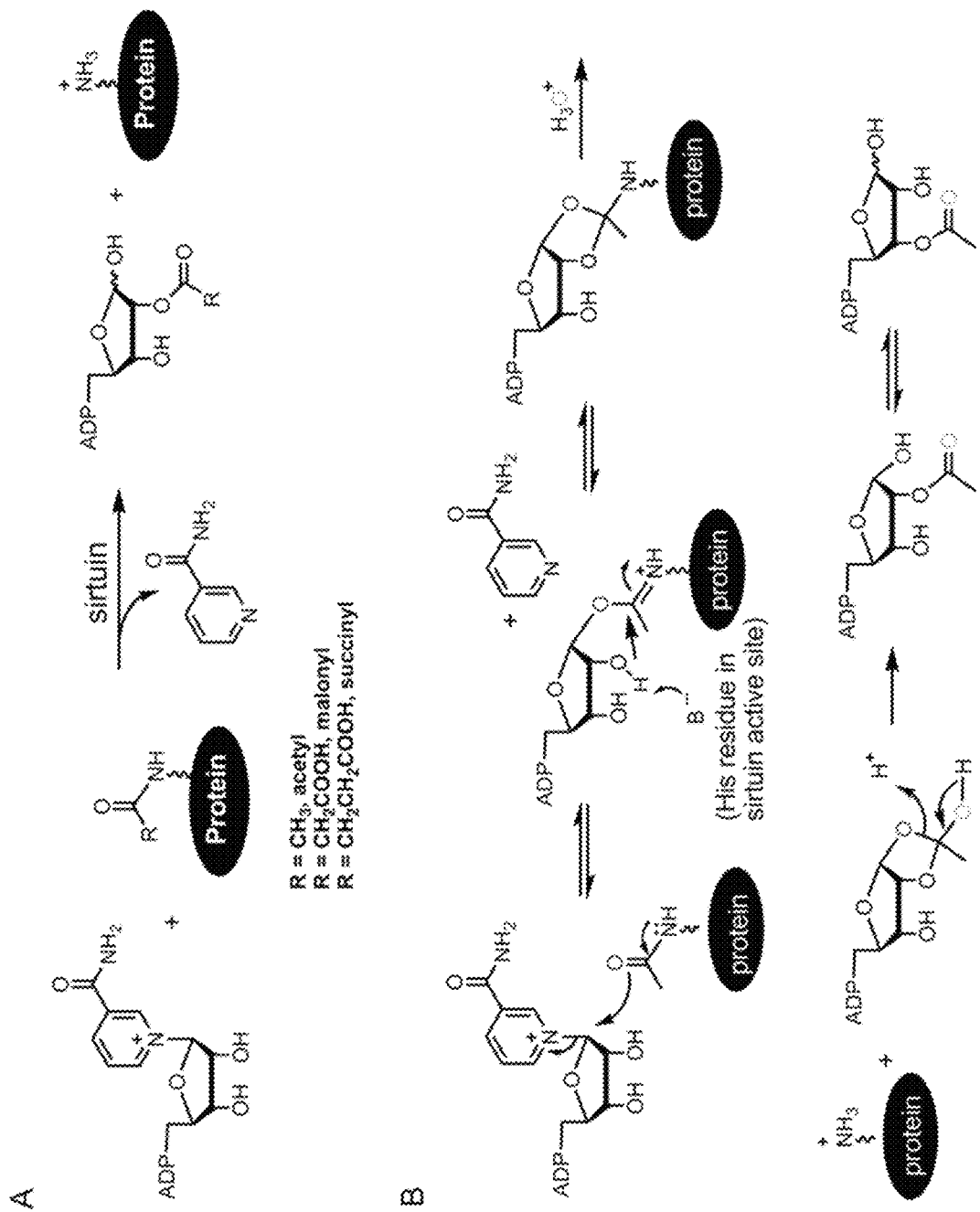
FIGS. 6A-6B. (A) The sirtuin-catalyzed NAD-dependent deacylation reaction is shown, and the reaction generates O-acyl-ADP-ribose. (B) Mechanism of sirtuin-catalyzed NAD-dependent deacetylation.
Figure 7C:
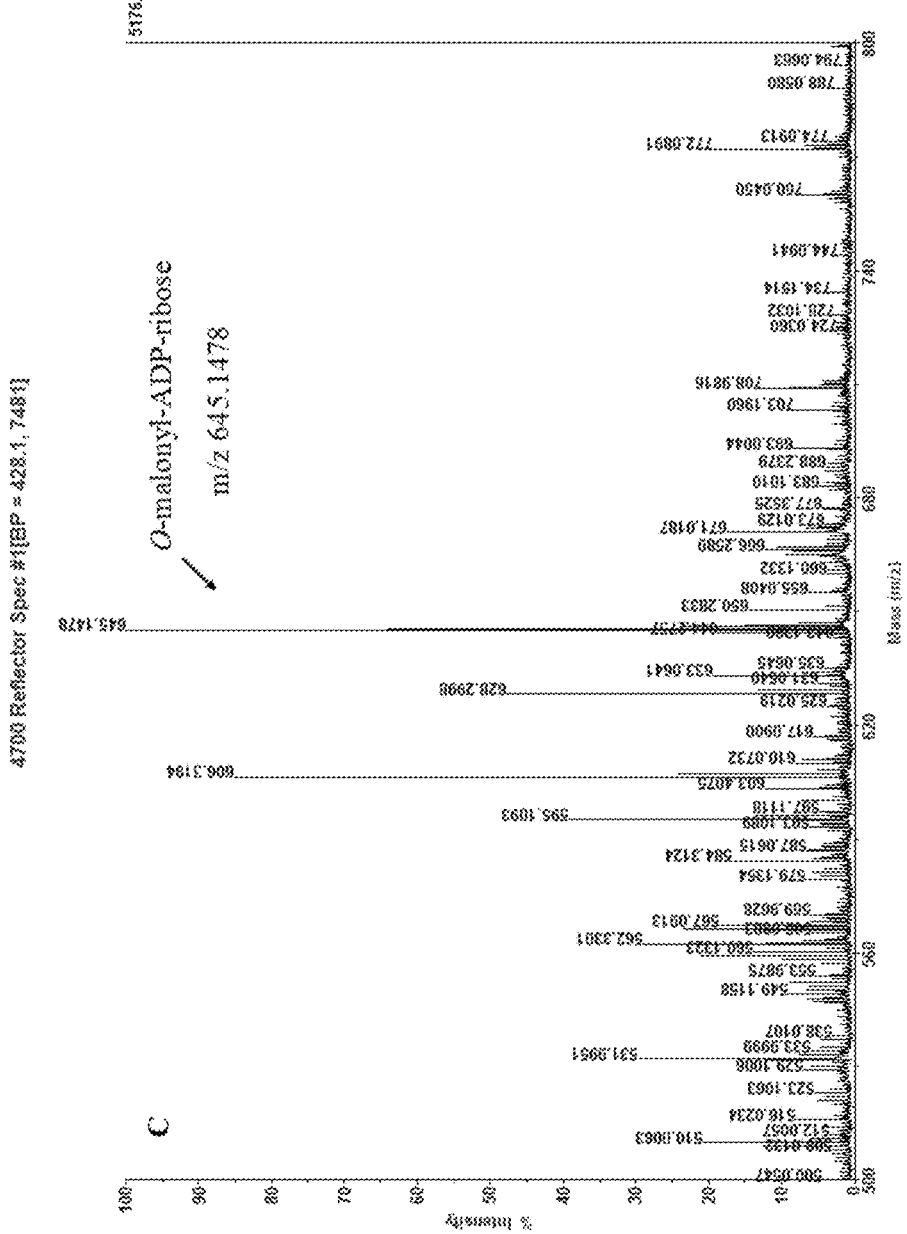
Figure 7D:
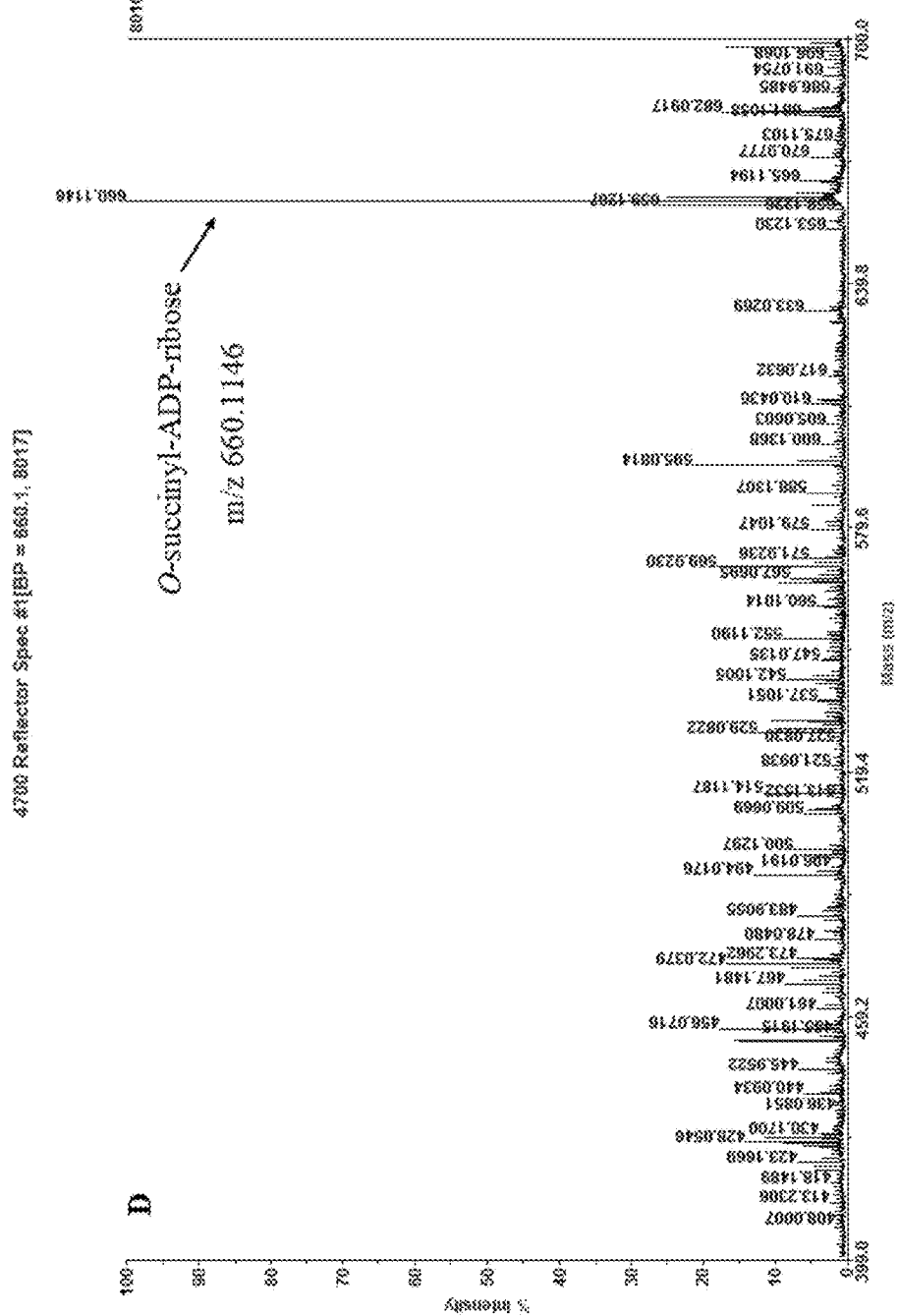
Figure 8:
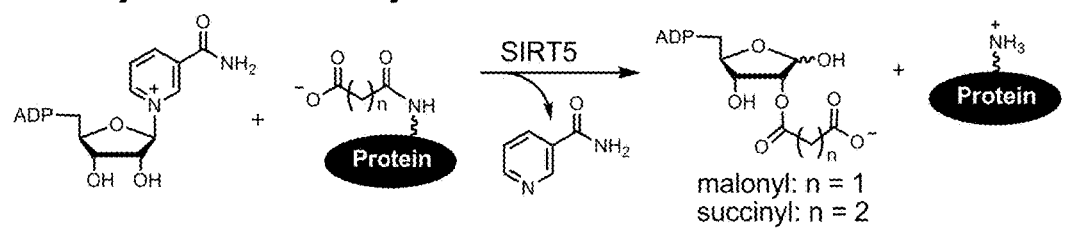
FIG. 8. Demalonylation and desuccinylation reactions catalyzed by Sirt5.

The deacetylation mechanism of sirtuins has been well studied (FIG. 6B) (A. A. Sauve, et al., *Annu. Rev. Biochem.* 75:435 (2006); A. A. Sauve et al., *Biochemistry* 40:15456 (2001); W. F. Hawse et al., *Structure* 16:1368 (2008)). If Sirt5 uses the same mechanism to catalyze demalonylation and desuccinylation, O-malonyl-ADPR (O-Ma-ADPR) or O-succinyl-ADPR (O-Su-ADPR) should be produced in the reactions. These products were indeed detected by mass spectroscopy (FIG. 7A-7D). As controls, the reactions of Sirt1 with malonyl and succinyl peptides did not generate these products (FIG. 7A-7B, grey lines). The formation of O-Ma-ADPR and O-Su-ADPR can also be detected using $^{32}$P-NAD, as described in FIG. 4A. Therefore, the mechanism for Sirt5-catalyzed desuccinylation/demalonylation (FIG. 8) is similar to the deacetylation mechanism of Class I Sirtuins.

The $k_{cat}$ and $K_m$ values for Sirt5-catalyzed deacetylation, demalonylation, and desuccinylation were determined (Table 2) with three different peptide sequences.

TABLE 2

The kinetic parameters of Sirt5 on acetyl,
malonyl, and succinyl peptides with different sequences.

| Peptide | Activity | $k_{cat}$ (s$^{-1}$) | Peptide $K_m$ (μM) | $k_{cat}/K_m$ (s$^{-1}$M$^{-1}$) |
|---|---|---|---|---|
| H3 K9 (4-13 + WW*) | deacetylation | ND | ND (>750) | 7.8 |
| | demalonylation | 0.037 ± 0.003 | 6.1 ± 2.8 | 6.1 × 10$^3$ |
| | desuccinylation | 0.025 ± 0.002 | 5.8 ± 2.7 | 4.3 × 10$^3$ |
| GDH K503 (498-509 + WW*) | deacetylation | ND | ND (>750) | <2** |
| | demalonylation | 0.014 ± 0.001 | 8.7 ± 1.3 | 1.6 × 10$^3$ |
| | desuccinylation | 0.028 ± 0.002 | 14 ± 4 | 2.0 × 10$^3$ |
| ACS2 K628 (623-632 + WW*) | deacetylation | ND | ND (>750) | 18 |
| | demalonylation | 0.079 ± 0.008 | 150 ± 40 | 5.2 × 10$^2$ |
| | desuccinylation | 0.268 ± 0.051 | 450 ± 150 | 6.0 × 10$^2$ |

*Two tryptophan residues were added at the C-terminal of the peptide to facilitate the detection by UV-Vis absorption during the HPLC assay.
**No activity. The value is estimated based on the detection limit.

With all three peptide sequences, the catalytic efficiencies for demalonylation and desuccinylation ($k_{cat}/K_m$ from 520 to 6100 s$^{-1}$M$^{-1}$) are much (29 to >1000 fold) higher than that for deacetylation. The demalonylation/desuccinylation efficiency of Sirt5 is comparable to the deacetylation efficiency of Sirt1 ($k_{cat}/K_m$ 1000 s$^{-1}$M$^{-1}$, Table 1). These kinetics studies provide further support that the desuccinylase and demalonylase activities of Sirt5 are more efficient than its deacetylase activity.

To obtain structural information about the recognition of succinyl/malonyl groups, a crystal structure of Sirt5 in complex with a succinyl peptide and NAD was obtained. The structure (FIG. 2D) showed that the carboxylate from succinyl interacts with Tyr102 and Arg105, consistent with what was predicted based on the structure of Sirt5 with CHES bound (FIG. 2C). Changing Arg105 to Met significantly decreased the $k_{cat}/K_m$ and increased the $K_m$ of Sirt5 for desuccinylation (Table 3). Changing Tyr102 to Phe did not affect the $k_{cat}/K_m$ much, but significantly increased the $K_m$ for desuccinylation. In contrast, the deacetylase activity was not affected. These data confirm that Tyr102 and Arg105 are important for binding succinyl and malonyl groups.

TABLE 3

The kinetic parameters of mutant Sirt5 on H3K9 acetyl and succinyl peptides

| | | $k_{cat}$ (s$^{-1}$) | $K_m$ for peptide (μM) | $k_{cat}/K_m$ (s$^{-1}$M$^{-1}$) |
|---|---|---|---|---|
| Sirt5 | deacetylation | ND* | ND (>750)* | 2 |
| | desuccinylation | 0.029 ± 0.002 | 41 ± 11 | 710 |
| Sirt5 H158Y | deacetylation | no activity observed | no activity observed | — |
| | desuccinylation | ND* | ND (>750)* | 75 |
| Sirt5 Y102F | deacetylation | ND* | ND (>750)* | 2 |
| | desuccinylation | ND* | ND (>750)* | 397 |
| Sirt5 R105M | deacetylation | ND* | ND (>750)* | 0.5 |
| | desuccinylation | ND* | ND (>750)* | 0.9 |

*The $k_{cat}$ and $K_m$ values cannot be determined because the V versus [S] plot is linear ($K_m$ is much greater than the highest substrate concentration tested, 750 μM). Thus only $k_{cat}/K_m$ value can be obtained.

Example 3

Detection of Succinyl Lysine from Bovine Liver Mitochondrial Proteins Using the $^{32}$P-NAD Assay Bovine liver mitochondria was isolated as previously described (C. Frezza, et al, *Nat. Protoc.* 2:287 (2007)). Mitochondria from 5 g bovine liver was lysed for 30 min at 4° C. in ice-cold lysis buffer (25 mM Tris-HCl pH 8.0, 50 mM NaCl, 0.1% Triton X-100) containing protease cocktail inhibitor (P8340, Sigma). The supernatants were collected and exchanged to 25 mM Tris-HCl (pH 8.0) with 50 mM NaCl using centrifugal filter (MILLIPORE, Billerica, Mass.) to get rid of endogenous NAD. The extracts were stored at −80° C. For trypsin digestion, 1.5 mg of the bovine liver mitochondria proteins or BSA (used as the control) was dissolved in 6 M urea, 60 mM Tris-HCl (pH 8.0), 15 mM DTT in a reaction volume of 450 μL. The solution was heated at 95° C. for 15 min and then cooled to room temperature. Then 22.5 μL of 1M iodoacetamide (final concentration ~50 mM) was added and the mixture was incubated at room temperature with gentle mixing for 1 h. Then 3.6 mL of 50 mM Tris-HCl (pH 7.4) with 1 mM CaCl$_2$ was added to the reaction mixture to lower the urea concentration to 0.75 M. Finally, 150 μL of 100 μg/mL modified trypsin (Promega Corporation, Madison, Wis.) was added and the reaction mixture was incubated at 37° C. for 12 h. After quenching the reaction by adding 65 μL 10% TFA to pH 2~3, the digested peptides were desalted by using Sep-Pak C18 cartridge 1 cc/50 mg (Waters Corporation, Milford, Mass.) and lyophilized.

To detect the acyl-ADPR compounds formed in sirtuin-catalyzed deacylation reactions, reactions were performed in 10 μL solutions with 1 μCi$^{32}$P-NAD (ARC Inc., ARP 0141, 800 Ci/mmol, 0.125 μM), 50 mM Tris-HCl pH 8.0, 150 mM NaCl, 10 mM DTT. The acyl peptide substrates used were 100 μM H3K9 acetyl, malonyl, or succinyl peptide, 2 μg calf thymus histones (Roche Applied Science, Indianapolis, Ind.), 20 μg bovine liver mitochondrial peptides, or 20 μg BSA peptides. The reactions were incubated with 1 μM Sirt5 or Sirt1 at 37° C. for 1 h. CD38 catalytic domain was used to generate ADPR as a control. A total of 0.5 μL of each reaction were spotted onto silica gel TLC plates and developed with 7:3 ethanol:ammonium bicarbonate (1 M aqueous solution). After development, the plates were air-dried and exposed to a PhosphorImaging screen (GE Healthcare, Piscataway, N.J.). The signal was detected using a STORM860 phosphorimager (GE Healthcare, Piscataway, N.J.).

Affinity Purification of Lysine-Succinyl Peptides and Protein Identification

Flag-Sirt5 (25 μg) was bound onto 100 μL anti-Flag M2 affinity gel (A2220, Sigma) by incubation at 4° C. in NETN buffer (50 mM Tris-HCl, pH 8.0, 100 mM NaCl, 1 mM EDTA, 0.5% NP40) for 2 hr (S. C. Kim et al., *Mol. Cell* 23: 607 (2006)). The supernatant was removed and the gel was washed three times with NETN buffer. The tryptic mitochondria peptides (~1 mg) obtained above were resolubilized in 0.5 mL NETN buffer and insoluble particles were removed by centrifugation at 10,000×g for 10 min. Affinity purification was carried out by incubating the peptides with Flag-Sirt5 bound anti-Flag M2 affinity gel at 4° C. for 3 h with gentle shaking. The gel was washed three times with 1 mL of NETN buffer and twice with ETN buffer (50 mM Tris-HCl, pH 8.0, 100 mM NaCl, 1 mM EDTA). The bound peptides were eluted three times with 100 µL of 0.1% TFA. The elutions were combined and lyophilized. The resulting peptides were cleaned using C18 ZipTips (Millipore, Bedford, Mass.) according to the manufacturer's instructions, prior to LC-MS/MS analysis performed at the Proteomic and MS Facility of Cornell University. Tandem mass spectra were searched against NCBI-nr database with MASCOT search engine (Matrix Science, London, UK) using acetyl, malonyl, and succinyl lysine as modifications.

Detection of Lysine Succinylation on CPS1 Peptides Using the $^{32}$P-NAD Assay

The CPS1 band was cut from a SDS-PAGE gel of the bovine liver mitochondria lysate. The protein was in-gel digested with trypsin and extracted and desalted as follows. The gel band was washed in 100 µL water for 5 min, followed by 100 µL 100 mM Ammonium bicarbonate: acetonitrile (1:1) for 10 min and finally 50 µL acetonitrile for 5 min. The acetonitrile was then discarded and the gel band was allowed to dry in the ventilated fume hood for 5-10 min. The gel slice was then rehydrated with 15 µL trypsin solution (10 µg/mL modified trypsin in 1 mM HCl) on ice for 30 min. The trypsin solution was topped with 10 µL 50 mM Ammonium bicarbonate with 10% acetonitrile. The digestion reactions were kept at 30° C. for 12 h. The resulting solution was acidified with formic acid (1% in final). The trypsin digested peptides were extracted twice with 30 µl of 50% acetonitrile with 0.2% TFA (45 min incubation at room temperature followed by 5 min sonication). The third extraction was with 30 µl of 90% acetonitrile with 0.2% TFA (5 min). All the extracts were combined and lyophilized. When dried, the peptides were dissolved in 12 µl of 0.1% TFA and desalted by ZipTips (Millipore, Bedford, Mass.). The desalted peptides were lyophilized again and reconstituted in water. The GDH peptides from in-gel digestion and the histone peptides from in-solution digestion were prepared as described above. The $^{32}$P-NAD assays were carried out as described above. To lower the detection limit, higher concentrations of Sirtuins were used. Sirt5 was used at a final concentration of 52 µM and the Hst2 was used at 24 µM. The sample peptides were used at a concentration of 0.3 µg/µl and the control peptides were at 20 µM.

Results. Protein Lysine Succinylation Exists in Mammalian Proteins.

Protein lysine malonylation has not been previously reported. Protein lysine succinylation was reported to occur on E. coli homoserine trans-succinylase (R. Rosen et al., FEBS Letters 577:386 (2004)). As mentioned above, Sirt5-catalyzed demalonylation/desuccinylation generates O-Ma-ADPR or O-Su-ADPR. When protein/peptide extracts from cells are incubated with Sirt5 and $^{32}$P-NAD, if $^{32}$P-labeled O-Ma-ADPR or O-Su-ADPR is produced, it would suggest that malonyl/succinyl lysine is present.

Figure 4:
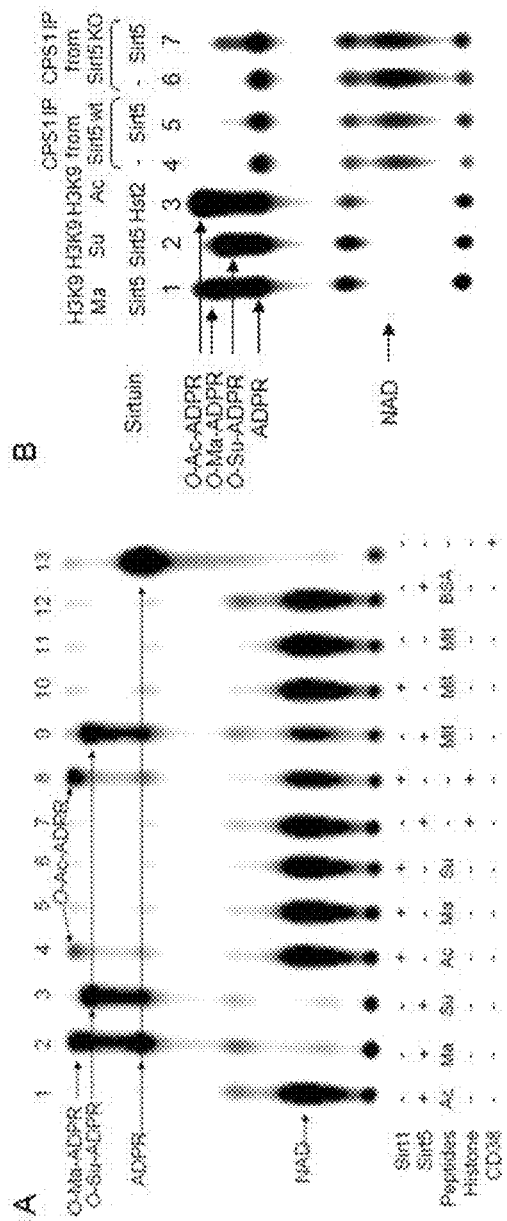
FIGS. 4A-B. (A) Succinyl lysine residues exist in bovine liver mitochondria. Sirt5-catalyzed hydrolysis of malonyl and succinyl peptides can be detected using $^{32}$P-NAD, which forms $^{32}$P-labeled O-Ma-ADPR (lane 2) and O-Su-ADPR (lane 3). No reaction occurred with acetyl peptide (lane 1). The formation of O-Ac-ADPR catalyzed by Sirt1 was detected when histones were used as the sources of acetyl lysine (lane 8) or H3K9 acetyl peptide (lane 4). O-Su-ADPR is formed when the trypsin-digested bovine liver mitochondria peptides were incubated with $^{32}$P-NAD and Sirt5 (lane 9), but not with Sirt1 (lane 10), suggesting that succinyl lysine residues are present in the bovine liver mitochondria extracts. The control with BSA peptides and Sirt5 did not generate O-Su-ADPR (lane 12). CD38 can hydrolyze NAD to generate ADPR and is used to generate the standard $^{32}$P-ADPR spot in lane 13. (B) Deletion of Sirt5 increases CPS1 succinylation level in mouse liver. CPS1 was immunoprecipitated from either wt or Sirt5 KO livers and the level of succinylation was detected using the $^{32}$P-NAD. Synthetic acetyl, malonyl and succinyl peptides were used to generate the reference points O-Ac-ADPR, O-Ma-ADPR and O-Su-ADPR, respectively.
Figure 5:
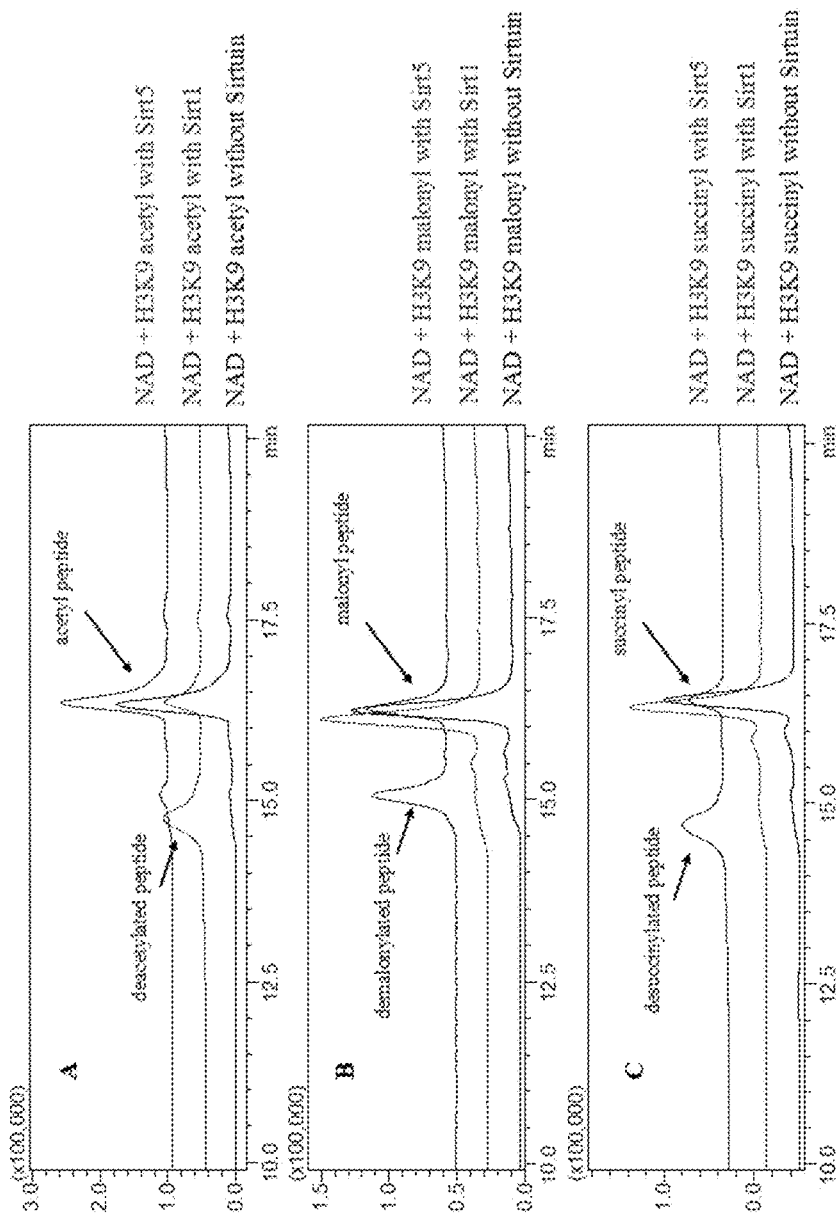
FIGS. 5A-5C. Sirt1 and Sirt5-catalyzed (A) deacetylation, (B) demalonylation and (C) desuccinylation of H3 K9 peptides were examined by HPLC (monitored at 215 nm). A longer HPLC column was used to better separate the acyl peptide and deacylated peptide. The results further confirmed that Sirt1 has better deacetylase activity, while Sirt5 has better demalonylase and desuccinylase activity.

To test whether Sirt5-catalyzed formation of O-Ma-ADPR and O-Su-ADPR can be detected using $^{32}$P-NAD, H3K9 acetyl, malonyl, and succinyl peptides were incubated with Sirt5 or Sirt1 in the presence of $^{32}$P-NAD. The small molecule products generated were then separated by thin-layer chromatograph (TLC) and detected by autoradiography. With the malonyl and succinyl peptide, Sirt5 consumed all the NAD molecules in 1 h (FIG. 4A, lanes 2 and 3). However, with the acetyl peptide, essentially no NAD was consumed (lane 1). Incubation of the acetyl peptide or full length calf thymus histones with Sirt1 led to the formation of O-Ac-ADPR (FIG. 4A, lanes 4 and 8). Histones were better substrates for Sirt1 than the short peptide, since the O-Ac-ADPR spot was stronger when histones were used in the reaction (lane 8). The O-Su-ADPR spot was separated from the O-Ac-ADPR and O-Ma-ADPR spots. These results suggest that Sirt5-catalyzed formation of O-Su-ADPR from the hydrolysis of succinyl peptides can be detected using $^{32}$P-NAD.

The $^{32}$P-NAD assay was then used to detect whether succinyl lysine is present in bovine liver mitochondrial proteins. Bovine liver mitochondria were used because Sirt5 is known to localize to mitochondria (E. Michishita, et al., Mol. Biol. Cell 16: 4623 (2005)). When bovine liver mitochondrial peptides were treated with Sirt5 and $^{32}$P-NAD, the formation of O-Su-ADPR was detected (FIG. 4A, lane 9), similar to the result obtained with synthetic succinyl peptide (lane 3), suggesting that bovine liver mitochondrial proteins contain succinyl lysine. Control reactions with Sirt1 (FIG. 4A, lane 10), without Sirtuins (lane 11), or with BSA peptides (lane 12) did not produce O-Su-ADPR or O-Ac-ADPR. The formation of O-Su-ADPR when bovine liver mitochondrial peptides were incubated with Sirt5 and NAD was further confirmed by LC-MS/MS (m/z 657, [M-2H]$^-$).

To identify succinylated proteins, succinyl peptides from bovine liver mitochondria were affinity purified using a FLAG-tagged Sirt5 (Sirt5-FLAG) and then identified by LC-MS/MS. Three succinylated proteins were identified: HMG-CoA synthase 2 (HMGCS2), thiosulfate sulfurtransferase, and aspartate aminotransferase. The sites of succinyl modification were identified by MS/MS. To identify more succinylated proteins, four mitochondrial enzymes purified from animal tissues were purchased: GDH, malate dehydrogenase, citrate synthase, and pyruvate dehydrogenase. Using LC-MS/MS, lysine succinylation was found to be present in three of the four enzymes: GDH, malate dehydrogenase, and citrate synthase (Table 4). Thus, lysine succinylation occurs to mammalian mitochondrial proteins.

TABLE 4

Examples of acetyl, malonyl, and succinyl peptides from mitochondrial extracts

| Proteins | Modified peptides |
|---|---|
| Malate dehydrogenase | 1 230-IQEAGTEVVK(succinyl)AK-241 (SEQ ID NO: 4)<br>2 230-IQEAGTEVVK(malonyl)AK-241 (SEQ ID NO: 5) |
| Citrate synthase | 3 74-GMK(succinyl)GLVYETSVLDPDEGIR-92 (SEQ ID NO: 6) |
| GDH | 4 524-TAMK(acetyl)YNLGLDLR-535 (SEQ ID NO: 7)<br>5 524-TAMK(malonyl)YNLGLDLR-535 (SEQ ID NO: 8)<br>6 524-TAMK(succinyl)YNLGLDLR-535 (SEQ ID NO: 9) |

Protein Lysine Malonylation Exists in Mammalian Proteins.

Neither the $^{32}$P-NAD assay (FIG. 4A) nor the Sirt5-FLAG affinity purification followed by LC-MS/MS identified any malonyl peptides. However, LC-MS/MS identified three malonyl lysine residues on commercial bovine liver GDH and two malonyl lysine residues from commercial malate dehydrogenase (Table 4). Interestingly, malonylation was found to occur on the same lysine residues that are also succinylated and/or acetylated (see Table 4, peptides 2-3 and 4-6). These data demonstrate that protein lysine malonylation exists in mammalian cells.

Sirt5 Can Remove Succinyl Groups from CPS1.

To demonstrate that the desuccinylase or demalonylase activity of Sirt5 is physiologically relevant, research focused on the reported Sirt5 target, carbamoyl phosphate synthase 1 (CPS1). It was reported that Sirt5 can modulate the activity of CPS1 via Sirt5's deacetylase activity (T. Nakagawa, et al., *Cell* 137:560 (2009)). Given that the demalonylase/desuccinylase activity of Sirt5 is much higher than the deacetylase activity, Sirt5 demalonylase or desuccinylase activity is more likely to be physiologically relevant. Consistent with this, trypsin-digested CPS1 peptides from bovine liver mitochondria was found to contain succinyl lysine based on the $^{32}$P-NAD assay.

Example 4

Generation of Sirt5 Deficient Mouse Line

Sirt5 +/+ and −/− mice were generated at the Institut Clinique de la Souris (Strasbourg, France). Briefly, exon 4 of Sirt5 locus was flanked with loxP sites using standard genetic engineering and gene targeting procedures. The resulting Sirt5 floxed mice were bred with CMV-Cre transgenic mice to generate germline Sirt5 deficient (Sirt5 −/−) mice and control Sirt5 +/+ mice. The absence of Sirt5 mRNA in different tissues of Sirt5 −/− mice was confirmed by Q-RT-PCR analysis and the loss of Sirt5 protein expression was verified by western blot using an anti-Sirt5 antibody (Abcam ab62740).

Detection of Succinylation Level on CPS1 from Sirt5 wt and KO Mouse Livers Using the $^{32}$P-NAD Assay.

The 29-week-old male Sirt5 +/+ and −/− littermates were fasted overnight (from 6:00 PM to 10:00 AM) and then provided with free access to food for four hours prior to sacrifice. Liver tissues were rapidly removed, snap-frozen with liquid nitrogen, and stored at −80° C. for analysis. The liver samples were first broken into small pieces, and then homogenized in 1 mL of the lysis buffer (50 mM Tris-HCl pH 8.0, 150 mM NaCl, 2 mM EDTA, 0.1% NP-40, 10% glycerol). The crude lysates were incubated at 4° C. on shaker for 30 min then centrifuged at 10000 g, 4° C. for 10 min. The concentration of the lysate was determined by Bradford assay.

The lysate with total protein of 200 μg was incubated with 3 μl of the CPS1 antibody (Abcam ab3682) at 4° C. for 60 min. 40 μl of the Protein A/G agarose beads (Santa Cruz Biotechnology sc-2003) was then added and incubated at 4° C. overnight. The beads were washed 3 times in Tris buffer (25 mM Tris-HCl pH 8.0, 50 mM NaCl, 0.1% NP-40). The beads with the immunopurified CPS1 was incubated with 1 μCi $^{32}$P-NAD and 50 mM Tris-HCl pH 8.0, 150 mM NaCl, 10 mM DTT. The Sirt5 was used at the concentration of 10 μM and Hst2 was used at 1 μM. The control peptides were used all at 20 μM concentration. The reaction was incubated at 37° C. for 1 h. 1.8 μL sample was loaded onto the TLC plate. Separation by TLC and detection by autoradiography was performed as described above.

Results.

To confirm that Sirt5's demalonylase/desuccinylase does function in vivo, a Sirt5 knockout (KO) mouse strain was generated using standard technology. Consistent with earlier reports (T. Nakagawa, et al., *Cell* 137:560 (2009)), no overt clinical phenotype was observed in the Sirt5 KO mice. CPS1 was immunoprecipitated from wild type and Sirt5 KO mouse liver extracts and incubated with recombinant Sirt5 and $^{32}$P-NAD. More O-Su-ADPR was formed with CPS1 from Sirt5 KO mouse (FIG. 4B, lane 7) than with CPS1 from wt mouse (FIG. 4B, lane 5). These results suggest that Sirt5 deletion increased the level of lysine succinylation on CPS1 in vivo and thus the desuccinylase activity is physiologically relevant.

Example 5

General Methods.

Reagents were obtained from Aldrich or Acros in the highest purity available and used as supplied. LCMS was carried out on a SHIMADZU LCMS-QP8000α with a Sprite TARGA C18 column (40×2.1 mm, 5 μm, Higgins Analytical, Inc., Mountain View, Calif.) monitoring at 215 and 260 nm. Solvents used in LCMS were water with 0.1% formic acid and acetonitrile with 0.1% formic acid.

Synthesis of Fmoc-Lys(Succinyl)-AMC.

Fmoc-Lys(Boc)-OH (1 g, 2.14 mmol) and 7-amino-4-methylcoumarin (AMC, 380 mg, 2.14 mmol) were dissolved in pyridine (12 mL). At −20° C., phosphorus oxychloride (0.4 mL) was added to the above mixture and the mixture was warmed to room temperature (RT). After 1 h at RT, the reaction was poured into ice water (120 mL). The mixture was extracted with EtOAc (100 ml×3). The combined organic layers were washed with water, 2 N HCl, water, 5% NaHCO$_3$ solution and brine, dried over anhydrous Na$_2$SO$_4$, filtered, and concentrated in vacuum to yield a yellow residue. The crude Fmoc-Lys(Boc)-MCA was dissolved in dichloromethane (6 mL) and then TFA was added (6 mL) to remove Boc. After 10 mins of stirring at RT, the reaction was concentrated by vacuum. Subsequently, menthol was added to the mixture and the mixture was vacuumed again until the excess of TFA was gone, yielding a yellow residue. The crude Fmoc-Lys-AMC and succinic anhydride were dissolved in pyridine (20 mL). The reaction was stirred for 2 hours at RT. The reaction was concentrated and then 1 N HCl was added to the residue. The mixture was extracted with EtOAc (100 ml×3). The combined organic layers were washed with brine, dried over anhydrous Na$_2$SO$_4$, filtered, and concentrated in vacuum to yield a yellow residue. Flash chromatography (9% MeOH/CH$_2$Cl$_2$) of the residue yielded Fmoc-Lys(Succinyl)-MCA as a white solid (1.3 g, 75% yield from Fmoc-Lys(Boc)-OH). LCMS (ESI) calculated for C$_{35}$H$_{35}$N$_3$O$_8$ [MH$^+$]=626.5, observed=626.0.

Synthesis of AMC-Succinyl Peptides.

Fmoc-Lys(succinyl)-AMC (125 mg, 0.2 mmol) was first coupled to trityl choloride resin (100 mg, 0.1 mmol). The peptide synthesis was carried out using standard Fmoc chemistry with O-benzotriazol-N,N,N',N'-tetramethyluronium hexafluorophosphate/1-hydroxybenzotriazol (HBTU/HOBt) protocol. To cleave the peptide from the solid support, the resin was suspended in a 1/1/8 (by volume) mixture of acetic acid/trifluoroethanol/CH$_2$Cl$_2$ for 30 mins at RT. The resin was removed by filtration and the filtrate was concentrated in vacuum. For removal of protecting groups, the above residue was treated with TFA (2 mL) for 4 hours. The crude peptides were purified by reverse phase HPLC on BECKMAN COULTER System Gold 125P solvent module & 168 Detector with a TARGA C18 column (250×20 mm, 10 μm, Higgins Analytical, Inc., Mountain View, Calif.) monitoring at 215 nm. Mobile phases used were 0.1% aqueous TFA (solvent A) and 0.1% TFA in acetonitrile (solvent B). Peptides were eluted with a flow rate of 10 mL/min with the following gradient: 0% solvent B for 5 min, then 0% to 25% solvent B over 25 min. The identity and purity of the peptides were verified by LCMS. KQTAR (SuK)-AMC peptide (SEQ ID NO:10), LCMS (ESI) calculated for C$_{44}$H$_{69}$N$_{13}$O$_{13}$ [MH$^+$]=988.5, observed=987.8.

ISGASE(SuK)-AMC peptide (SEQ ID NO:11), LCMS (ESI) calculated for $C_{42}H_{61}N_9O_{16}$ [MH$^+$]948.4, observed=948.0.

Synthesis of AMC-Acetyl Peptides.

Fmoc-Lys(acetyl)-OH (82 mg, 0.2 mmol) was first coupled with trityl choloride resin (100 mg, 0.1 mmol). The peptides were synthesized using standard Fmoc chemistry with O-benzotriazol-N,N,N',N'-tetramethyluronium hexafluorophosphate/1-hydroxybenzotriazol (HBTU/HOBt) protocol. The peptides were cleaved from the resin with 1/1/8 (by volume) of acetic acid/trifluoroethanol/CH$_2$Cl$_2$ for 30 minutes at RT and concentrated in a vacuum. The remaining acetic acid was removed as an azeotrope with hexane to give protected peptides with free C-terminal carboxyl acid. The residue was dissolved in a solution of CH$_2$Cl$_2$ (2 mL) and pyridine (50 µL). AMC (63 mg, 0.36 mmol) and DCC (N, N'-Dicyclohexylcarbodiimide, 64 mg, 0.31 mmol) were added to the above mixture. After stifling at RT overnight, the reaction was filtered and the filtrate was concentrated in vacuum. To remove protecting groups, the peptides were treated with TFA (2 mL) for 4 hours. The crude peptides were purified by reverse phase HPLC on BECKMAN COULTER System Gold 125P solvent module & 168 Detector with a TARGA C18 column (250×20 mm, 10 µm, Higgins Analytical, Inc., Mountain View, Calif.) monitoring at 215 nm. Mobile phases used were 0.1% aqueous TFA (solvent A) and 0.1% TFA in acetonitrile (solvent B). Peptides were eluted with a flow rate of 10 mL/min with the following gradient: 0% solvent B for 5 min, then 0% to 25% solvent B over 25 min. The identity and purity of the peptides were verified by LCMS. KQTAR (AcK)-AMC peptide (SEQ ID NO: 12), LCMS (ESI) calculated for $C_{42}H_{67}N_{13}O_{11}$ [MH$^+$]=930.5, observed=930.7. ISGASE(AcK)-AMC peptide (SEQ ID NO: 13), LCMS (ESI) calculated for $C_{40}H_{59}N_9O_{14}$ [MH$^+$]=890.4, observed=890.5.

Synthesis of AMC-Free Lys Peptides.

Fmoc-Lys(Boc)-OH (94 mg, 0.2 mmol) was first coupled with trityl choloride resin (100 mg, 0.1 mmol) and the rest of the synthesis was similar to the synthesis of AMC-acetyl peptides. KQTARK-AMC peptide (SEQ ID NO: 14), LCMS (ESI) calculated for $C_{40}H_{65}N_{13}O_{10}$ [MH$^+$]=888.5, observed=888.0. ISGASEK-AMC peptide (SEQ ID NO: 15), LCMS (ESI) calculated for $C_{38}H_{57}N_9O_{13}$ [MH$^+$]=848.4, observed=848.7.

Sirt5 Fluorogenic Assay with KQTAR(SuK)-AMC.

SirT5 (1 µM) was incubated with KQTAR(SuK)-AMC (SEQ ID NO: 10) peptide (0.3 mM), NAD (0.5 mM) in Tris-HCl buffer (pH 7.4, 20 mM) containing dithiothreitol (DTT, 1 mM) in a 60 µL reaction for 16 hours at 37° C. Then trypsin (1 µg) and CaCl$_2$ (1 mM) were added and the reaction were incubated for 14 hours at 37° C. The reactions were diluted with 50 µL water. The mixture (100 µL) was transferred to 96 well plate and the fluorescence was recorded by BIO-TEK® Synergy HT plate reader (Optics Position: Top, Sensitivity: 50, Excitation at the wavelength of 360 nm and Emission at the wavelength of 460 nm).

Monitoring Trypsin-Catalyzed Hydrolysis of AMC-Free Lys Peptides by LCMS.

The KQTARK-AMC (SEQ ID NO: 14) peptide (0.3 mM, 60 µL reactions) was incubated with different amount of trypsin (0 µg, 1 µg, 2 µg or 5 µg), Tris-HCl buffer (pH 7.4, 50 mM) and CaCl$_2$ (1 mM) for 14 hours at 37° C. The reactions were stopped with 200 mM HCl and 320 mM acetic acid, analyzed by LCMS. Traces detected the masses of KQTARK-AMC (SEQ ID NO: 14) peptide (m/z 808.0), KQTAR (SEQ ID NO: 16) peptide (m/z 603.0) and lysine-AMC (m/z 304.0). The results showed that the KQTARK-AMC (SEQ ID NO: 14) peptide was cleaved to KQTAR (SEQ ID NO: 16) and lysine-AMC, but cleavage of lysine-AMC was not efficient.

Monitoring Sirt5-Catalyzed Desuccinylation of ISGASE (SuK)-AMC by HPLC.

Sirt5 was incubated with ISGASE(SuK)-AMC (SEQ ID NO: 11) peptide (0.3 mM), NAD (0.5 mM) in Tris-HCl buffer (pH 7.4, 20 mM) with DTT (1 mM) in a 60 µL reaction at 37° C. for 4 hours. The reactions were stopped with 200 mM HCl and 320 mM acetic acid, analyzed by HPLC with a reverse phase C18 column (250×4.6 mm, 90 A, 10 µm, GraceVydac, Southborough, Mass.), with a linear gradient of 0% to 20% B for 10 min (1 mL/min). Product quantification was based on the area of absorption monitored at 215 nm, assuming hydrolysis of the succinyl group does not affect the absorption.

Assaying Sirt5 Activity on ISGASE(SuK)-AMC in the Fluorogenic Assay.

SirT5 (1 µM) was incubated with ISGASE(SuK)-AMC (SEQ ID NO:11) peptide (0.3 mM), NAD (0.5 mM) in Tris-HCl buffer (pH 7.4, 20 mM) with DTT (1 mM) in 60 µL reactions for 4 hours at 37° C. Then trypsin (1 µg) and CaCl$_2$ (1 mM) were added and the reactions were incubated for 3 hours at 37° C. The reactions were the diluted with 50 µL water. The mixture (100 µL) was transferred to 96 well plate and the fluorescence was recorded by BIO-TEK® Synergy HT plate reader (Optics Position: Top, Sensitivity: 50, Excitation at the wavelength of 360 nm and Emission at the wavelength of 460 nm).

Screening for Sirt5 Inhibitors with ISGASE(SuK)-AMC in the Fluorogenic Assay.

The procedure was the same as described above (Assaying Sirt5 activity on ISGASE(SuK)-AMC in the fluorogenic assay), except that different compounds (30 µM) were included in the reactions. In the desuccinylation step, Sirt5 was added last to initiate the desuccinylation reaction.

Assaying Sirt1, 2, 3, and 5 Activity on ISGASE(AcK)-AMC in the Fluorogenic Assay.

The procedure was the same as described above (Assaying Sirt5 activity on ISGASE(SuK)-AMC in the fluorogenic assay), except that a different acyl peptide was used and the incubation time with different sirtuins is 10 hrs.

Secondary Screening for Sirt5-Specific Inhibitors Using Sirt2 and ISGASE(AcK)-AMC.

SirT2 (1 µM) was incubated with ISGASE(AcK)-AMC (SEQ ID NO:13) peptide (0.3 mM), inhibitors (30 µM), NAD (0.5 mM) in Tris-HCl buffer (pH 7.4, 20 mM) containing dithiothreitol (DTT, 1 mM) in a 60 µL reaction for 4 hours at 37° C. Then trypsin (1 µg) and CaCl$_2$ (1 mM) were added and the reaction were incubated for 3 hours at 37° C. The reactions were diluted with 50 µL water. The mixture (100 µL) was transferred to 96 well plate and the fluorescence was recorded by BIO-TEK® Synergy HT (Optics Position: Top, Sensitivity: 50, Excitation at the wavelength of 360 nm and Emission at the wavelength of 460 nm).

Results.

It was thought that thiosuccinyl and thiomalonyl peptides should inhibit Sirt5 desuccinylase and demalonylase activities by forming a stalled covalent intermediate. Because other sirtuins do not recognize malonyl and succinyl lysine peptides, thiomalonyl and thiosuccinyl peptides should be Sirt5-specific inhibitors. To test this hypothesis, a H3K9 thiosuccinyl (H3K9 TSu) peptide was synthesized. Thiosuccinyl was chosen because succinyl lysine has a lower $K_m$ value for Sirt5.

Figure 9:
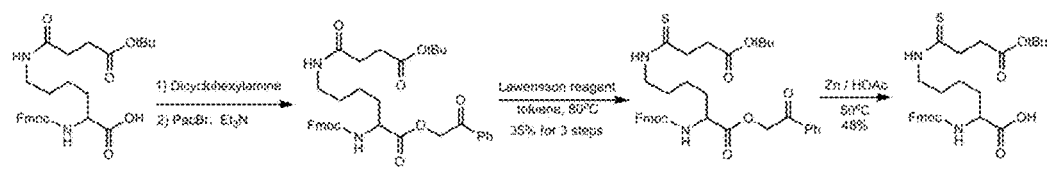
FIG. 9. The synthesis of a protected thiosuccinyl Lys compound, which is used to make H3K9 TSu peptide.

The H3K9 TSu peptide was synthesized by making a protected thiosuccinyl lysine compound first (FIG. 9). The thiosuccinyl lysine compound was then used in standard Fmoc solid phase peptide synthesis to give the desired H3K9 TSu peptide, KQTAR(TSuK)STGGKA (SEQ ID NO: 17). As a control, an H3K9 thioacetyl peptide (H3K9 TAc) was also synthesized.

Figure 10:
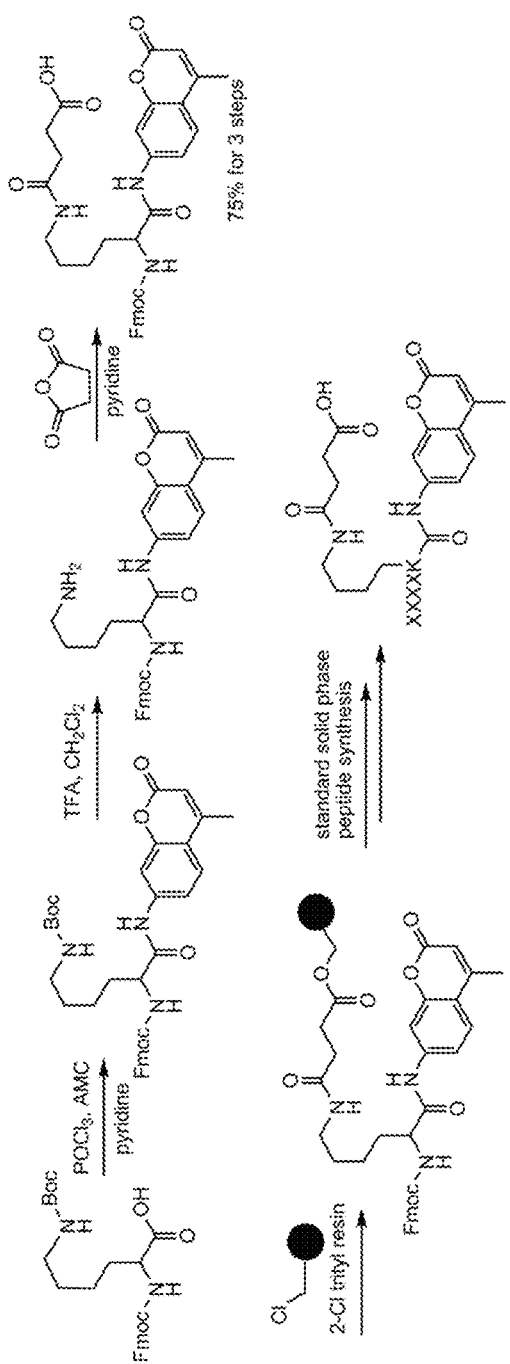
FIG. 10. The synthesis of AMC-succinyl peptides.

The synthetic route to the AMC-succinyl peptide is shown in FIG. 10. H3K9 succinyl peptide with AMC attached (KQTAR(SuK)-AMC) (SEQ ID NO: 10) was synthesized. The H3K9 succinyl peptide was chosen because originally a similar succinyl peptide was used to assay the activity of Sirt5. Initial assays with this fluorogenic succinyl peptide showed that the fluorescence (360 nm excitation, 480 nm emission) in the presence of Sirt5 only increased ~3-fold compared with the control reaction without Sirt5 (3600 and 1200 relative fluorescence unit for reactions with and without Sirt5, respectively). To analyze why KQTAR(SuK)-AMC was an inefficient substrate for assaying Sirt5 in the fluorogenic assay, KQTARK-AMC peptide was synthesized and monitored for hydrolysis by trypsin. It turned out that trypsin cleaved the peptide after the Arg residue very fast, yielding Lys-AMC, which can only be slowly hydrolyzed by trypsin to release the fluorescent AMC.

Based on the above finding, another AMC-succinyl peptide, ISGASE(SuK)-AMC (SEQ ID NO:11), was made using a peptide sequence derived from glutamate dehydrogenase. This peptide does not have an Arg or Lys residue before the succinyl Lys residue, and thus was efficiently digested by trypsin once the succinyl group is removed. For controls, ISGASE(AcK)-AMC (SEQ ID NO: 13) and ISGASEK-AMC (SEQ ID NO: 15) peptides were synthesized. The ISGASEK-AMC peptide was first used to check whether it can be efficiently digested by trypsin to release the fluorescent AMC molecule. The results showed that 1 μg of trypsin can hydrolytically release essentially all the AMC molecules in 4 hrs. Using HPLC, the efficiency of Sirt5-catalyzed desuccinylation with 300 μM of ISGASE(SuK)-AMC was also monitored. In 2 hrs, 7.3%, 17%, and 36% of the succinyl peptide are desuccinylated with 1, 2, and 5 μM of Sirt5, respectively. For comparison, the KQTAR(SuK)-AMC (SEQ ID NO:10) peptide is hydrolyzed by Sirt5 with similar efficiency (10% and 60% hydrolysis by 1 and 5 μM of Sirt5 in 3 hrs).

Figure 11:
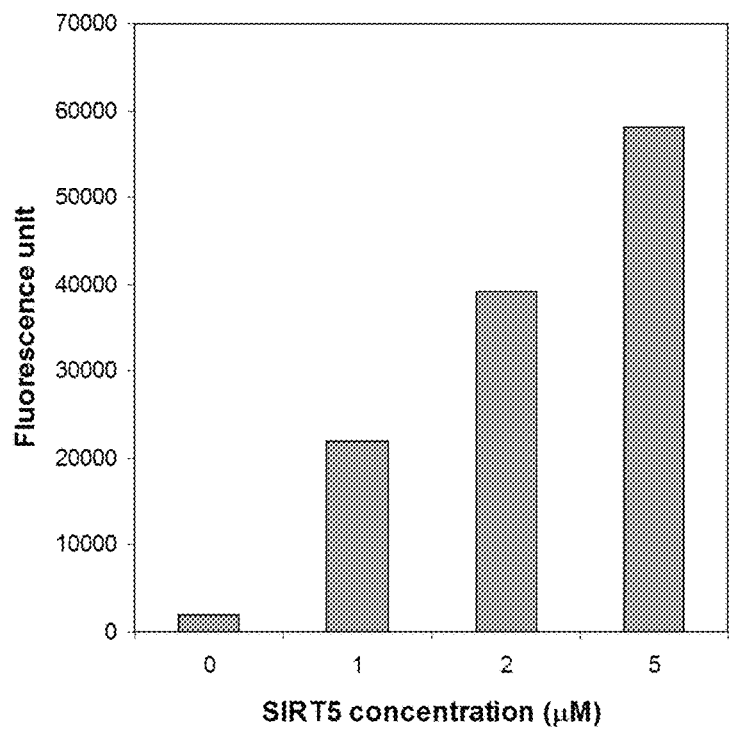
FIG. 11. ISGASE(SuK)-AMC is a substrate for Sirt5. The ISGASE(SuK)-AMC peptide was incubated with or without Sirt5 for 4 hrs and then with 1 µg trypsin for 3 hrs. Compared with the negative control without Sirt5, the fluorescence was increased 11, 20, and 26-fold by 1, 2, and 5 µM of Sirt5.
Figure 12:
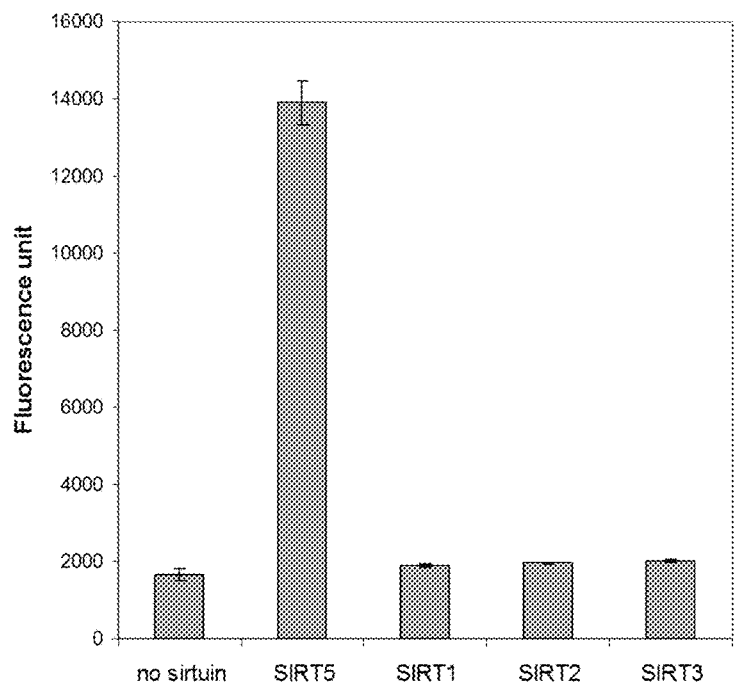
FIG. 12. ISGASE(SuK)-AMC is not a substrate for Sirt1, 2, and 3. The ISGASE(SuK)-AMC peptide was incubated with 1 µM of different sirtuins for 4 hrs and then with 1 µg trypsin for 3 hrs. Compared with the negative control without sirtuins, the fluorescence was only increased by Sirt5.

Having confirmed that ISGASE(SuK)-AMC (SEQ ID NO:11) is a good substrate for Sirt5 and trypsin, it was then tested in the fluorogenic assay. A 4 hour incubation with 1 μM Sirt5 followed by 3 hrs incubation with 1 μg of trypsin increased the fluorescence 11-fold compared with the control without Sirt5. Increasing the concentration of Sirt5 to 5 μM led to a 26-fold increase in fluorescence (FIG. 11). In contrast, no fluorescence increase was observed when Sirt1, 2, or 3 was used instead of Sirt5 (FIG. 12). These results demonstrate that the ISGASE(SuK)-AMC peptide is a suitable fluorogenic substrate for a Sirt5 activity assay.

Figure 13:
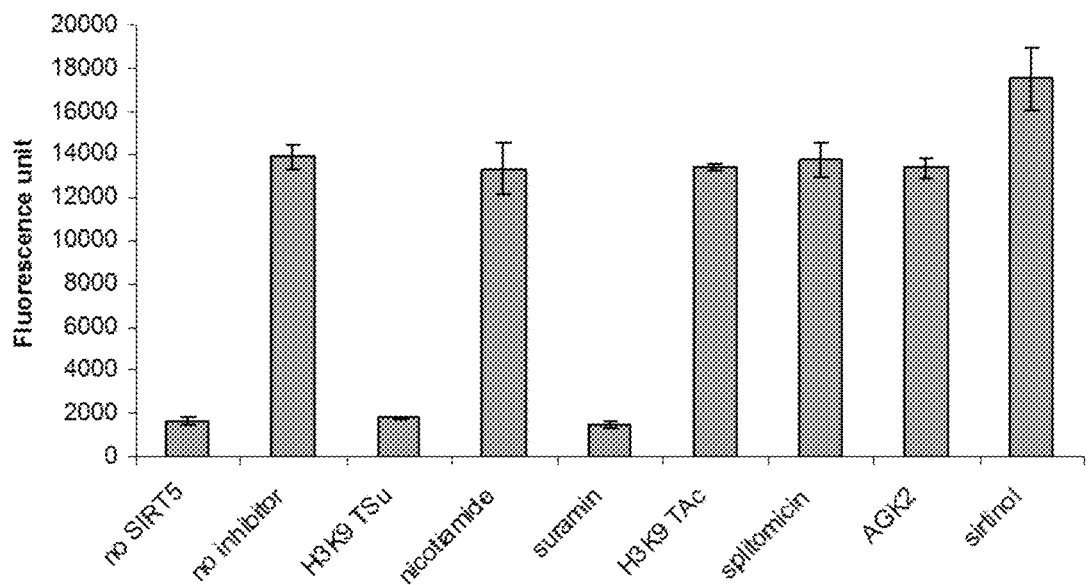
FIG. 13. Using the fluorogenic substrate ISGASE(SuK)-AMC to screen Sirt5 inhibitors. Reactions without Sirt5 and with Sirt5 but without added small molecules were used as controls. All small molecules were used at 30 µM concentration. H3K9 TSu and suramin showed significant inhibition of Sirt5.

Next, the fluorogenic assay was tested to identify compounds that can inhibit Sirt5 (FIG. 13). Compounds that are reported to be sirtuin inhibitors, including suramin (L. Gao et al., *Journal of Chromatography B* 853:303 (2007)); AGK2 (E. Michishita, et al., *Mol. Biol. Cell* 16: 4623 (2005)); sirtinol (K.-H. Kim, *Ann. Rev. Nutr.* 17:77 (1997)); and splitomicin were tested. In addition to these reported compounds, a thiosuccinyl peptide, H3K9 TSu, which can selectively inhibit Sirt5 with $IC_{50}$ value of 5 μM, was tested. Suramin was reported to inhibit Sirt5's deacetylase activity with $IC_{50}$ value of 22 μM (L. Gao et al., *Journal of Chromatography B* 853:303 (2007)). The $IC_{50}$ value for suramin on the desuccinylase activity of Sirt5 using an HPLC-based assay was similar. Other compounds were not efficient at inhibiting Sirt5, with $IC_{50}$ values >100 μM. Using 30 μM concentrations, these compounds were tested for ability to inhibit Sirt5 in the fluorogenic assay. As shown in FIG. 13, the fluorescence was close to background level in the presence of 30 μM of H3K9 TSu and suramin. In contrast, other compounds did not significantly decrease the fluorescence. These results are consistent of the $IC_{50}$ values of these compounds for Sirt5. Thus, the H3K9 TSu peptide is not only the first Sirt5-specific inhibitor, but also the most potent Sirt5 inhibitor reported thus far.

The inhibition of Sirt1, 2, 3, and 5 with the H3K9 TSu peptide and H3K9 TAc peptide was tested. The $IC_{50}$ values are shown in Table 5. All assays were carried out under identical enzyme (1 μM) and substrate (0.3 mM acyl peptide, 0.5 mM NAD) concentrations.

TABLE 5

$IC_{50}$ values of H3K9 TSu and TAc peptides for different sirtuins.

| | $IC_{50}$ (μM) | | | | | |
|---|---|---|---|---|---|---|
| | H3K9 TSu | H3K9 TAc | nicotin-amide | AGK2 | suramin | sirtinol |
| Sirt1 | >100 * | 1 | ND (<50[14]) | ND (>40[10]) | ND (0.3[15]) | ND (131[16]) |
| Sirt2 | >100 * | 2 | ND (32[17]) | ND (3.5[10]) | ND (1.2[15]) | ND (38[18]) |
| Sirt3 | >100 * | 2 | ND | ND (>40[10]) | ND | ND |
| Sirt5 | 5 | >100 * | 150 | 120 | 25 (22[19]) | >100 * |

* No inhibition at 100 μM.
ND: not determined in this study. However, the $IC_{50}$ values have been reported for some of the inhibitors on Sirt1-3. Available reported values are shown in parentheses.

H3K9 TSu did not inhibit Sirt1-3 even at 100 μM concentration, but inhibited Sirt5 with $IC_{50}$ value of 5 μM. In contrast, the H3K9 TAc peptide inhibited Sirt1-3 with $IC_{50}$ values of 1-2 μM, but did not inhibit Sirt5 at 100 mM. The results demonstrate that H3K9 TSu peptide is a Sirt5-specific inhibitor.

Figure 14:
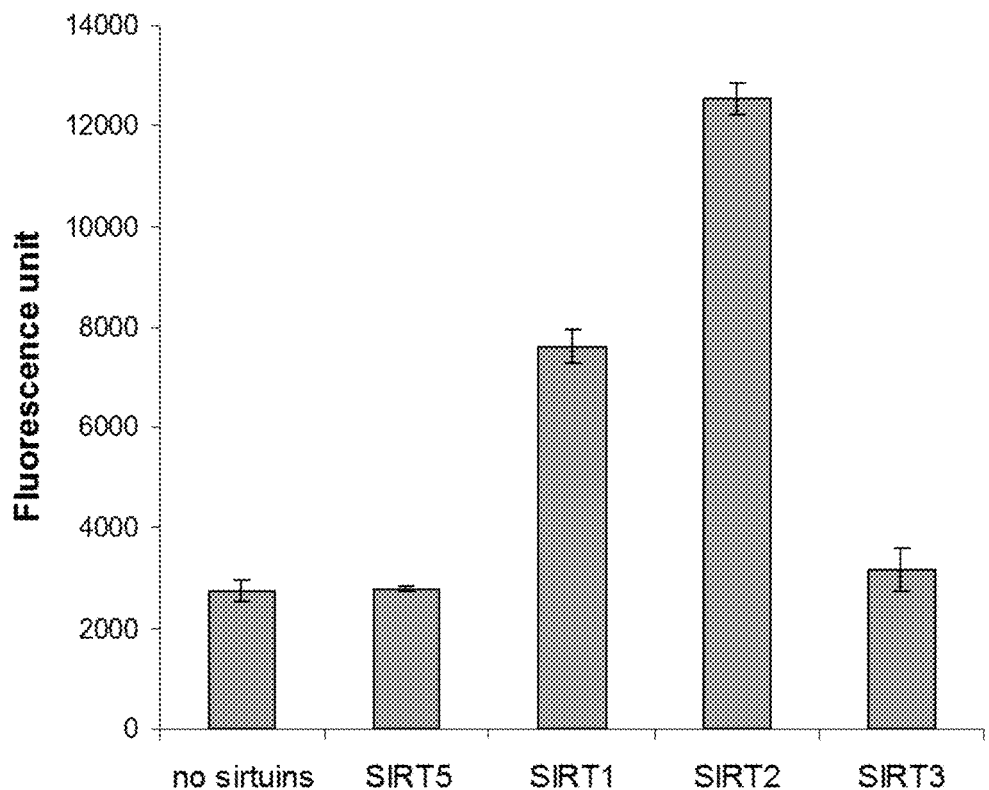
FIG. 14. ISGASE(AcK)-AMC is a substrate for Sirt2. The ISGASE(AcK)-AMC peptide was incubated with 1 µM of different sirtuins for 10 hrs and then with 1 µg trypsin for 3 hrs. Compared with the negative control without sirtuins, Sirt2 increased the fluorescence the most while Sirt5 and Sirt3 did not significantly increase the fluorescence.
Figure 15:
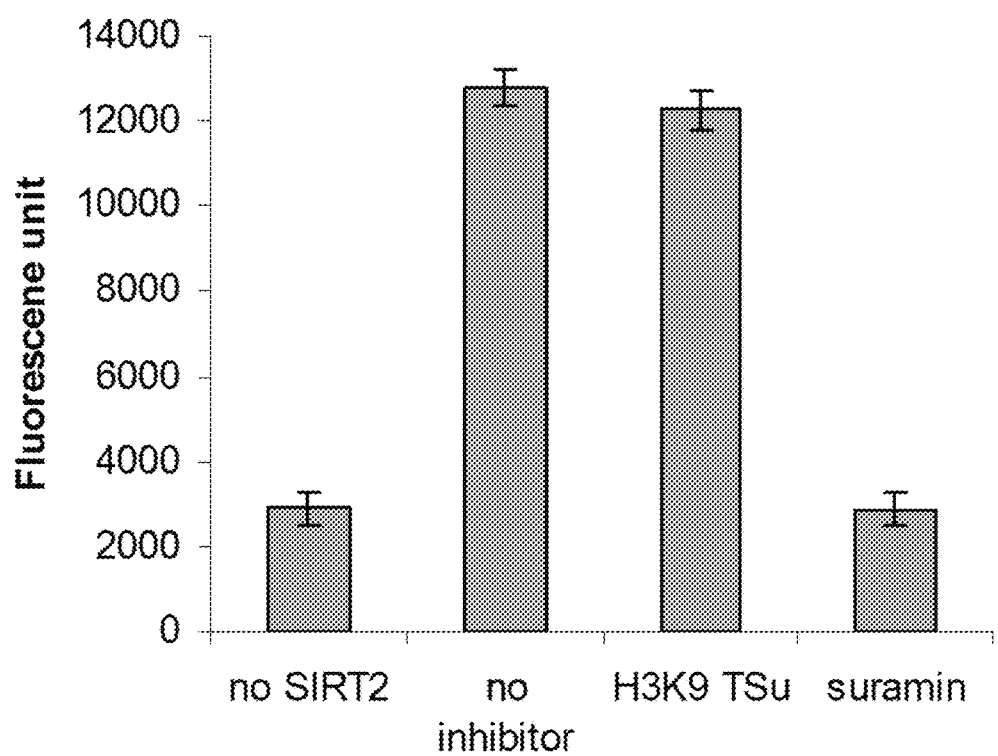
FIG. 15. A screen with ISGASE(AcK)-AMC and Sirt2 establishes H3K9 TSu, but not suramin, as a Sirt5-specific inhibitor.

Sirt5 assay with AMC-succinyl peptide can be coupled with a secondary assay with AMC-acetyl peptide for Sirt1/2/3 to eliminate compounds that can also inhibit Sirt1/2/3. ISGASE(AcK)-AMC (SEQ ID NO:13) peptide was used to test whether H3K9 TSu and suramin can inhibit Sirt1/2/3. ISGASE(AcK)-AMC peptide is a substrate for Sirt2 (FIG. 14). Using Sirt2 and ISGASE(AcK)-AMC, the two inhibitors obtained with Sirt5 and ISGASE(SuK)-AMC (SEQ ID NO:11) were tested. The results (FIG. 15) showed that H3K9 TSu did not significantly decrease the fluorescence produced by Sirt2, while suramin decreased the fluorescence to almost background level. The result is consistent with the finding that H3K9 TSu is a Sirt5-specific inhibitor, and demonstrates that the Sirt5 assay with AMC-succinyl peptide coupled with a Sirt1/2/3 assay with AMC-acetyl peptide can be used to screen for compounds that selectively modulate Sirt5 activity.

What is claimed is:

1. A method for identifying a modulator of Sirt5 demalonylase or desuccinylase activity, comprising:
   providing a candidate compound;
   providing a substrate comprising a malonyl or succinyl lysine linked to an indicator moiety;
   contacting the substrate with Sirt5 in the presence of the candidate compound and in the presence of nicotinamide adenine dinucleotide (NAD) under conditions for Sirt5 to demalonylate or desuccinylate the substrate;
   contacting the demalonylated or desuccinylated substrate with a cleavage agent that cleaves the linkage between the lysine and the indicator moiety to release the indicator moiety, thereby generating a detectable signal; and
   correlating signal intensity with Sirt5 demalonylase or desuccinylase activity;
   wherein a change in Sirt5 demalonylase or desuccinylase activity in the presence of the candidate compound, relative to Sirt5 demalonylase or desuccinylase activity in the absence of the candidate compound, identifies the candidate compound as a modulator of Sirt5 demalonylase or desuccinylase activity.

2. The method of claim 1, wherein the substrate is a peptide comprising a malonyl or succinyl lysine covalently linked to the indicator moiety through a peptide bond.

3. The method of claim 2, wherein the cleavage agent is a proteolytic enzyme.

4. The method of claim 3, wherein the proteolytic enzyme is trypsin.

5. The method of claim 1, wherein the indicator moiety has fluorescent properties.

6. The method of claim 5, wherein the indicator moiety comprises a fluorophore which changes its emission wavelength upon the cleavage and release of the indicator moiety.

7. The method of claim 5, wherein the indicator moiety comprises a fluorophore and the substrate is also labeled with a quenching group, and upon cleavage from the substrate, the indicator moiety generates a fluorescent signal.

8. The method of claim 5, wherein the indicator moiety comprises a fluorophore which is one member of a donor-acceptor fluorophore pair and is attached to the carboxyl terminus of the lysine residue, and the other member of the pair is attached directly or indirectly to the amino terminus of the lysine residue.

9. The method of claim 8, wherein cleavage of the indicator fluorophore from the substrate reduces FRET-based signal intensity.

10. The method of claim 5, wherein the indicator moiety is AMC.

11. The method of claim 10, wherein the substrate is ISGASE(SuK)-AMC (SEQ ID NO: 11).

12. The method of claim 1, wherein the candidate compound is a small molecule.

13. The method of claim 12, wherein the candidate compound has the formula:

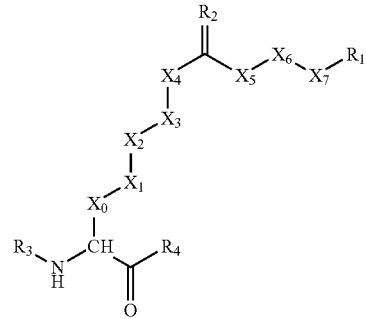

wherein:
R$_1$ is an anionic or ionizable group;
R$_2$ is selected from S, NR$_5$, and O, wherein R$_5$ is H, methyl, ethyl, isopropyl, phenyl, or benzyl;

when $R_1$ is carboxyl, then $R_2$ is not O, and when $R_2$ is O, then $R_1$ is not carboxyl;

$X_0$, $X_1$, $X_2$, $X_3$, $X_4$, $X_5$, $X_6$ and $X_7$ are independently selected from —$(CH_2)_n$—, wherein n represents 1, 2, or 3, —$NR_5$—, —O—, —S—, or a bond, provided that at least one of $X_0$-$X_4$ is not a bond, and at least one of $X_5$-$X_7$ is not a bond;

$R_3$ and $R_4$ are independently selected from H, hydrocarbon (R), amino acid, dipeptide, tripeptide, oligopeptide, protein, nucleobase, nucleotide, dinucleotide, trinucleotide, oligonucleotide, monosaccharide, disaccharide, oligosaccharide, and protecting groups or a combination thereof or modified form thereof.

14. The method of claim 1, further comprising testing the ability of the candidate molecule to affect deacetylation activity of any of Sirt 1, 2, or 3.

15. The method of claim 13, wherein $R_2$ is S.

* * * * *

```
                              SEQUENCE LISTING

<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Ile Ser Gly Ala Ser Glu Lys
1               5

<210> SEQ ID NO 2
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 2
agtcaggaat tcatggcagc cggggggtct                                          29

<210> SEQ ID NO 3
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 3
agtcagctcg agttacgtca ctttcttcct tttt                                     34

<210> SEQ ID NO 4
<211> LENGTH: 12
<212> TYPE: PRT
<213> ORGANISM: Bos taurus
<220> FEATURE:
<221> NAME/KEY: MOD_RES
<222> LOCATION: 10
<223> OTHER INFORMATION: SUCCINYLLYSINE

<400> SEQUENCE: 4

Ile Gln Glu Ala Gly Thr Glu Val Val Lys Ala Lys
1               5                   10

<210> SEQ ID NO 5
<211> LENGTH: 12
<212> TYPE: PRT
<213> ORGANISM: Bos taurus
<220> FEATURE:
<221> NAME/KEY: MOD_RES
<222> LOCATION: 10
<223> OTHER INFORMATION: MALONYLLYSINE

<400> SEQUENCE: 5

Ile Gln Glu Ala Gly Thr Glu Val Val Lys Ala Lys
1               5                   10

<210> SEQ ID NO 6
<211> LENGTH: 19
<212> TYPE: PRT
<213> ORGANISM: Bos taurus
```

```
<220> FEATURE:
<221> NAME/KEY: MOD_RES
<222> LOCATION: 3
<223> OTHER INFORMATION: SUCCINYLLYSINE

<400> SEQUENCE: 6

Gly Met Lys Gly Leu Val Tyr Glu Thr Ser Val Leu Asp Pro Asp Glu
1               5                   10                  15

Gly Ile Arg

<210> SEQ ID NO 7
<211> LENGTH: 12
<212> TYPE: PRT
<213> ORGANISM: Bos taurus
<220> FEATURE:
<221> NAME/KEY: MOD_RES
<222> LOCATION: 4
<223> OTHER INFORMATION: ACETYLLYSINE

<400> SEQUENCE: 7

Thr Ala Met Lys Tyr Asn Leu Gly Leu Asp Leu Arg
1               5                   10

<210> SEQ ID NO 8
<211> LENGTH: 12
<212> TYPE: PRT
<213> ORGANISM: Bos taurus
<220> FEATURE:
<221> NAME/KEY: MOD_RES
<222> LOCATION: 4
<223> OTHER INFORMATION: MALONYLLYSINE

<400> SEQUENCE: 8

Thr Ala Met Lys Tyr Asn Leu Gly Leu Asp Leu Arg
1               5                   10

<210> SEQ ID NO 9
<211> LENGTH: 12
<212> TYPE: PRT
<213> ORGANISM: Bos taurus
<220> FEATURE:
<221> NAME/KEY: MOD_RES
<222> LOCATION: 4
<223> OTHER INFORMATION: SUCCINYLLYSINE

<400> SEQUENCE: 9

Thr Ala Met Lys Tyr Asn Leu Gly Leu Asp Leu Arg
1               5                   10

<210> SEQ ID NO 10
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 6
<223> OTHER INFORMATION: SUCCINYLLYSINE, 7-AMINO-4-METHYLCOUMARIN
      ATTACHED

<400> SEQUENCE: 10

Lys Gln Thr Ala Arg Lys
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 7
<223> OTHER INFORMATION: SUCCINYLLYSINE, 7-AMINO-4-METHYLCOUMARIN
      ATTACHED

<400> SEQUENCE: 11

Ile Ser Gly Ala Ser Glu Lys
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 6
<223> OTHER INFORMATION: ACETYLLYSINE, 7-AMINO-4-METHYLCOUMARIN ATTACHED

<400> SEQUENCE: 12

Lys Gln Thr Ala Arg Lys
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 7
<223> OTHER INFORMATION: ACETYLLYSINE, 7-AMINO-4-METHYLCOUMARIN ATTACHED

<400> SEQUENCE: 13

Ile Ser Gly Ala Ser Glu Lys
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 6
<223> OTHER INFORMATION: 7-AMINO-4-METHYLCOUMARIN ATTACHED

<400> SEQUENCE: 14

Lys Gln Thr Ala Arg Lys
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 7
<223> OTHER INFORMATION: 7-AMINO-4-METHYLCOUMARIN ATTACHED
```

```
<400> SEQUENCE: 15

Ile Ser Gly Ala Ser Glu Lys
1               5

<210> SEQ ID NO 16
<211> LENGTH: 6
<212> TYPE: PRT
<213> ORGANISM: Artificial Sequence
<220> FEATURE:
<223> OTHER INFORMATION: synthetic peptide

<400> SEQUENCE: 16

Lys Gln Thr Ala Arg Lys
1               5

<210> SEQ ID NO 17
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 6
<223> OTHER INFORMATION: THIOSUCCINYLLYSINE

<400> SEQUENCE: 17

Lys Gln Thr Ala Arg Lys Ser Thr Gly Gly Lys Ala
1               5                   10
```